(12) United States Patent
Ozaki

(10) Patent No.: US 9,828,613 B2
(45) Date of Patent: Nov. 28, 2017

(54) ACYL-ACP THIOESTERASE

(71) Applicant: Kao Corporation, Chuo-ku, Tokyo (JP)

(72) Inventor: Tatsuro Ozaki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/897,049

(22) PCT Filed: Jun. 27, 2014

(86) PCT No.: PCT/JP2014/067137
§ 371 (c)(1),
(2) Date: Dec. 9, 2015

(87) PCT Pub. No.: WO2015/005139
PCT Pub. Date: Jan. 15, 2015

(65) Prior Publication Data
US 2016/0130615 A1    May 12, 2016

(30) Foreign Application Priority Data

Jul. 12, 2013  (JP) ................. 2013-146624

(51) Int. Cl.
| C12P 7/64 | (2006.01) |
| C12N 1/00 | (2006.01) |
| C12N 1/13 | (2006.01) |
| C12N 1/15 | (2006.01) |
| C12N 1/21 | (2006.01) |
| C12N 9/16 | (2006.01) |

(52) U.S. Cl.
CPC .............. *C12P 7/6409* (2013.01); *C12N 9/16* (2013.01); *C12P 7/6463* (2013.01); *C12Y 301/02014* (2013.01)

(58) Field of Classification Search
None
See application file for complete search history.

(56) References Cited

U.S. PATENT DOCUMENTS

| 2009/0317878 A1 | 12/2009 | Champagne et al. |
| 2011/0217743 A1 | 9/2011 | Yoshida et al. |
| 2015/0111264 A1 | 4/2015 | Ozaki et al. |
| 2015/0307860 A1 | 10/2015 | Ozaki et al. |
| 2017/0044580 A1 | 2/2017 | Sugihara et al. |
| 2017/0107545 A1 | 4/2017 | Tojo et al. |
| 2017/0114376 A1 | 4/2017 | Ozaki et al. |

FOREIGN PATENT DOCUMENTS

| JP | 7-501924 A | 3/1995 |
| JP | 11-505115 A | 5/1999 |
| JP | 2002-502263 A | 1/2002 |
| JP | 2014-132892 A | 7/2014 |
| JP | 2015-177771 A | 10/2015 |
| WO | WO 92/20236 A1 | 11/1992 |
| WO | WO 96/36719 A1 | 11/1996 |
| WO | WO 98/55633 A1 | 12/1998 |
| WO | WO 2011/108755 A1 | 9/2011 |
| WO | WO 2011/150410 A2 | 12/2011 |
| WO | WO 2012/061647 A2 | 5/2012 |
| WO | WO 2014/103930 A1 | 7/2014 |
| WO | WO 2015/133305 A1 | 9/2015 |
| WO | WO 2015/194628 A1 | 12/2015 |
| WO | WO 2016/021481 A1 | 2/2016 |

OTHER PUBLICATIONS

Zhang et al., "Efficient free fatty acid production in *Escherichia coli* using plant acyl-ACP thioesterases", Metabolic Engineer. 13:713-722, 2011.*
Sang, H., Mechanisms of Development 121:1179-1186, 2004.*
GenBank Database Accession No. AY835984, Sep. 2010, 2 pages.*
Excerpted file history, U.S. Appl. No. 14/646,895, § 371 Date: May 22, 2015, Non-Final Rejection dated Feb. 13, 2017, from the United States Patent and Trademark Office, Alexandria, VA.
International Search Report (ISR) for PCT/JP2014/067137; I.A. fd: Jun. 27, 2014, dated Sep. 2, 2014, from the Japanese Patent Office, Tokyo, Japan.
International Preliminary Report on Patentability (IPRP), Chapter I of the Patent Cooperation Treaty, including the Written Opinion for PCT/JP2014/067137; I.A. fd: Jun. 27, 2014, dated Jan. 12, 2016, from the International Bureau of WIPO, Geneva, Switzerland.
Excerpted file history, U.S. Appl. No. 14/646,895, § 371 Date: May 22, 2015, Applicant's preliminary amendment filed May 22, 2015 at the United States Patent and Trademark Office, Alexandria, VA.
Leggat, W. et al., " Analysis of an EST library from the dinoflagellate (*Symbiodinium* sp.) symbiont of reef-building corals," Journal of Phycology 43(5): 1010-1021, Oct. 2007, Wiley.
Zhang, H. et al., "Proof that Dinoflagellate Spliced Leader (DinoSL) is a Useful Hook for Fishing Dinoflagellate Transcripts from Mixed Microbial Samples: *Symbiodinium kawagutii* as a Case Study," Protist 164:510-527 (Jul. 2013; Epub: Jun. 14, 2013), Elsevier GmbH.
Voelker, T.A. et al., "Fatty acid biosynthesis redirected to medium chains in transgenic oilseed plants," Science 257:72-74, Jul. 1992, Am. Assoc. Adv. Sci, Washington, DC.
Gong, Y. et al., Characterization of a novel thioesterase (PtTE) from *Phaeodactylum tricornutum*, J. Basic Microbiology 51:666-672 (Dec. 2011), Wiley-Vch Verlag GmbH & Co. KGaA, Weinheim, Germany.
GenBank Accession No. EKU23063.1, Thioesterase superfamily member 4 [Nannochloropsis gaditana CCMP526], Radakovits, R. et al., direct submission, GenBank version EKU23063.1, GI:422295764, PLN Nov. 20, 2012, retrieved from the Internet, www.ncbi.nlm.nih.gov/protein/EKU23063.1?report=girevhist>, on Feb. 3, 2014.
GenBank Accession No. EKU23063.1, Thioesterase superfamily member 4 [Nannochloropsis gaditana CCMP526], Radakovits, R. et al., direct submission, GenBank version EKU23063.1, GI:422295764, PLN Nov. 20, 2012, last update Mar. 18, 2015, retrieved from the Internet, www.ncbi.nlm.nih.gov/protein/EKU23063.1?report=girevhist>, on Apr. 23, 2015.

(Continued)

*Primary Examiner* — David J Steadman
(74) *Attorney, Agent, or Firm* — Sterne, Kessler, Goldstein & Fox P.L.L.C.

(57) ABSTRACT

An acyl-ACP thioesterase consisting of an amino acid sequence of the $72^{nd}$ to $233^{rd}$ amino acids set forth in SEQ ID NO: 1, an acyl-ACP thioesterase gene encoding the protein, a transformant having the gene, and a method of producing a lipid using the transformant.

18 Claims, No Drawings

(56) References Cited

OTHER PUBLICATIONS

Mayer, KM et al., "Identification of amino acid residues involved in substrate specificity of plant acyl-ACP thioesterases using a bioinformatics-guided approach," BMC Plant Biol. Jan. 3, 2007;7:1, DOI: 10.1186/1471-2229-7-1, 11 pages, BioMed Central, London, England.
Nannochloropsis gaditana strain B-31 contig00219, whole genome shotgun sequence, [online], Feb. 14, 2014, database GenBank, AZIL01000370, [retrieval date Nov. 8, 2016], Carpinielli, E et al., direct submission, Internet<URL:http://www.ncbi.nlm.nih.gov/nuccore/AZIL01000370.
Radakovits, R. et al., "Draft genome sequence and genetic transformation of the oleaginous alga *Nannochloropsis gaditana*," Nature Communications (Feb. 21, 2012), vol. 3, Article No. 686, ten page (1-10), doi:10.1038/ncomms1688; and Corrigendum to correct the Title, Nature Communications vol. 4, Article No. 2356, Sep. 19, 2013; Nature Pub. Group, London, England).
Radakovits, R et al., "Genetic Engineering of Algae for Enhanced Biofuel Production," Eukaryot Cell, Apr. 2010; 9:486-501, American Society for Microbiology, Washington, DC.
Tojo, T. et al., "Kokoyashi Yurai Acyl-ACP Thioesterase wa Chusa Shibosan no Seisan ni Kan' yo suru," ("Characterization of Acyl-ACP thioesterase derived from coconut"), [online], 2012, Japan Society for Bioscience, Biotechnology, and Agrochemistry 2012 Nendo Taikai Topic Sho Happyo Bango: 2C10a02, [retrieval date Aug. 20, 2015 (Aug. 20, 2015) ], Internet<URL: http://www.jsbba.or.jp/wp-content/uploads/file/award/2012/topics/7_2C10a02.pdf, Dynacom Co., Ltd.
Yuan, L et al., "The catalytic cysteine and histidine in the plant acyl-acyl carrier protein thioesterases," J Biol Chem. Feb. 16, 1996;271(7):3417-3419, American Society for Biochemistry and Molecular Biology, Baltimore, MD.
Yuan, L et al., "Modification of the substrate specificity of an acyl-acyl carrier protein thioesterase by protein engineering," Proc Nat Acad Sci U S A. Nov. 7, 1995;92(23):10639-10643, National Academy of Sciences, Washington, DC.
International Search Report (ISR) for PCT/JP2013/084244; I.A. fd: Dec. 20, 2013, dated Feb. 18, 2014, the Japanese Patent Office, Tokyo, Japan.
International Preliminary Report on Patentability (IPRP) including the Written Opinion of the International Searching Authority (PCT Rule 44bis) for PCT/JP2013/084244; I.A. fd: Dec. 20, 2013, dated Jun. 30, 2015, by the International Bureau of WIPO, Geneva, Switzerland.
International Search Report (ISR) for PCT/JP2015/067581; I.A. fd Jun. 18, 2015, dated Sep. 1, 2015 from the Japan Patent Office, Tokyo, Japan.
International Preliminary Report on Patentability (IPRP), Chapter I of the Patent Cooperation Treaty, including the Written Opinion for PCT/JP2015/067581; I.A. fd Jun. 18, 2015, dated Dec. 20, 2016, by the International Bureau of WIPO, Geneva, Switzerland.
Excerpted file history, U.S. Appl. No. 14/646,895, § 371 Date: May 22, 2015, Applicant's amendment and reply filed Jul. 11, 2017, the United States Patent and Trademark Office, Alexandria, VA.
Excerpted file history, U.S. Appl. No. 15/317,345, § 371 Date: Dec. 8, 2016, Applicant's preliminary amendment filed Dec. 8, 2016, the United States Patent and Trademark Office, Alexandria, VA.
Excerpted file history, U.S. Appl. No. 15/110,635, § 371 Date: Jul. 8, 2016, Applicant's preliminary amendments filed Sep. 29, 2016 and Jul. 8, 2016, the United States Patent and Trademark Office, Alexandria, VA.
Excerpted file history, U.S. Appl. No. 15/317,347, § 371 Date: Dec. 8, 2016, Applicant's preliminary amendment filed Dec. 8, 2016, the United States Patent and Trademark Office, Alexandria, VA.
International Search Report (ISR) for PCT/JP2015/054960; I.A. fd: Feb. 23, 2015, dated May 26, 2015, the Japanese Patent Office, Tokyo, Japan.
International Preliminary Report on Patentability (IPRP) including the Written Opinion of the International Searching Authority (PCT Rule 44bis) for PCT/JP2015/054960; I.A. fd: Feb. 23, 2015, dated Sep. 6, 2016, by the International Bureau of WIPO, Geneva, Switzerland.
International Search Report (ISR) for PCT/JP2015/071666; I.A. fd: Jul. 30, 2015, dated Oct. 13, 2015, the Japanese Patent Office, Tokyo, Japan.
International Preliminary Report on Patentability (IPRP) including the Written Opinion of the International Searching Authority (PCT Rule 44bis) for PCT/JP2015/071666; I.A. fd: Jul. 30, 2015, dated Feb. 7, 2016, by the International Bureau of WIPO, Geneva, Switzerland.

\* cited by examiner

ACYL-ACP THIOESTERASE

TECHNICAL FIELD

The present invention relates to an acyl-ACP thioesterase, and a gene encoding the same. Further, the present invention relates to a transformant having the acyl-ACP thioesterase gene and a method of producing a lipid using the same.

BACKGROUND ART

Fatty acids are one of the principal components of lipids. In vivo, fatty acids are bonded to glycerin via an ester bond to form lipids such as triacylglycerol. Many animals and plants store and utilize fatty acids as an energy source. These fatty acids and lipids (fats and oils) stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts and alkylbenzenesulfonic acid salts are utilized as anionic surfactants, and polyoxyalkylene alkyl ethers, alkyl polyglycosides and the like are utilized as nonionic surfactants. These surfactants are used for detergents or disinfectants. As other higher alcohol derivatives, cationic surfactants such as alkylamine salts and mono- or dialkyl-quaternary amine salts are commonly used for fiber treatment agents, hair conditioning agents or disinfectants, and benzalkonium type quaternary ammonium salts are commonly used for disinfectants or antiseptics. Moreover, vegetable fats and oils are used also as raw materials of biodiesel fuels.

Fatty acids and lipids are widely used for various applications shown above. Therefore, it has been attempted to enhance the productivity of fatty acids or lipids in vivo by using plants and the like. Further, the applications and usefulness of fatty acids depend on the number of carbon atoms. Therefore, controlling of the number of carbon atoms of the fatty acids, namely, a chain length thereof has also been attempted. For example, a method of accumulating fatty acids having 12 carbon atoms by introducing an acyl-ACP thioesterase derived from *Umbellularia californica* (California bay) (Patent Literature 1, and Non-Patent Literature 1) has been proposed.

Recently, algae attract attention due to its usefulness in biofuel production. The algae can produce lipids that can be used as the biodiesel fuels through photosynthesis, and do not compete with foods. Therefore, the algae attract attention as next-generation biomass resources. Moreover, the algae are also reported to the effect that the algae have higher lipid productivity and accumulation ability in comparison with plants. For example, a method of collecting the fats and oils, and fatty acids from algae belonging to the genus *Symbiodinium* has been proposed in Patent Literature 2.

Research has started on a lipid synthesis mechanism of the algae and production technologies utilizing the mechanism, but unclear parts remain in many respects. For example, almost no report has been made so far on the above-mentioned acyl-ACP thioesterase derived from algae, either, and only limited examples of reports are made on Class Diatomea or the like (for example, Non-Patent Literature 2).

CITATION LIST

Patent Literatures

Patent Literature 1: JP-A-7-501924 ("JP-A" means unexamined published Japanese patent application)

Patent Literature 2: WO 2011/108755 A1

Non-Patent Literatures

Non-Patent Literature 1: Voelker T A, Worrell A C, Anderson L, Bleibaum J, Fan C, Hawkins D J, Radke S E, Davies H M., "Fatty acid biosynthesis redirected to medium chains in transgenic oilseed plants", Science. 1992 Jul. 3; 257 (5066), p. 72-74.

Non-Patent Literature 2: Yangmin Gong, Xiaojing Guo, Xia Wan, Zhuo Liang, Mulan Jiang, "Characterization of a novel thioesterase (PtTE) from Phaeodactylum tricornutum", Journal of Basic Microbiology, 2011 December, Volume 51, p. 666-672.

SUMMARY OF INVENTION

The present invention relates to a protein selected from the group consisting of the following (a) to (c):

(a) A protein consisting of an amino acid sequence of the $72^{nd}$ to $233^{rd}$ amino acids set forth in SEQ ID NO: 1;

(b) A protein consisting of an amino acid sequence having 70% or more identity with the amino acid sequence of the protein (a), and having acyl-ACP thioesterase activity; and (c) A protein containing the amino acid sequence of the protein (a) or (b), and having acyl-ACP thioesterase activity.

(Hereinafter, the protein is referred to as "the protein of the present invention" or "the acyl-ACP thioesterase of the present invention".)

The present invention also relates to a gene encoding the protein of the present invention, preferably a gene consisting of any one selected from the group consisting of the following DNAs (d) to (f):

(d) A DNA consisting of a nucleotide sequence of the $214^{th}$ to $699^{th}$ nucleotides set forth in SEQ ID NO: 2;

(e) A DNA consisting of a nucleotide sequence having 70% or more identity with the nucleotide sequence of the DNA (d), and encoding a protein having acyl-ACP thioesterase activity; and (f) A DNA containing the nucleotide sequence of the DNA (d) or the DNA (e), and encoding a protein having acyl-ACP thioesterase activity.

(Hereinafter, the gene is referred to as "the gene of the present invention" or "the acyl-ACP thioesterase gene of the present invention".)

The present invention also relates to a transformant obtained by introducing the gene of the present invention into a host (Hereinafter, referred to as "the transformant of the present invention").

The present invention also relates to a method of producing a lipid, containing the steps of:

culturing the transformant of the present invention in medium; and collecting a lipid from the resulting cultured product.

(Hereinafter, the method is referred to as "the method of producing a lipid of the present invention".)

The present invention also relates to a method of modifying a fatty acid composition in a lipid, containing introducing the gene of the present invention into a host.

Further, the present invention also relates to a method of enhancing productivity of a lipid, containing introducing the gene of the present invention into a host.

Other and further features and advantages of the invention will appear more fully from the following description.

MODE FOR CARRYING OUT THE INVENTION

The present invention relates to providing a novel acyl-ACP thioesterase derived from algae, and an acyl-ACP thioesterase gene encoding the same. Further, the present invention relates to providing a transformant having the gene. Furthermore, the present invention relates to providing a method of producing a lipid using the transformant.

The present inventors made extensive studies so as to search a novel acyl-ACP thioesterase derived from algae. As a result, they found a novel acyl-ACP thioesterase and an acyl-ACP thioesterase gene encoding the thioesterase derived from algae belonging to the genus *Symbiodinium*. The present invention was completed based on these findings.

The present invention can provide a novel acyl-ACP thioesterase and an acyl-ACP thioesterase gene encoding the same. The present invention can also provide a transformant having the acyl-ACP thioesterase gene. Further, the present invention can provide a method of producing a lipid using the transformant. The transformant and the production method of the present invention have the excellent productivity of lipids, and therefore they can be suitably used for the industrial production of fatty acids or lipids.

Hereinafter, the present invention will be explained.

In the present invention, the term "lipid(s)" covers simple lipids such as neutral lipids, wax, and ceramides; complex lipids such as phospholipids, glycolipids, and sulfolipids; and derived lipids such as fatty acids, alcohols, and hydrocarbons. In the present specification, "neutral lipid" means an ester of a fatty acid and glycerin. Specifically, "neutral lipid" means a monoglyceride, a diglyceride, and a triglyceride. In the present specification, "neutral lipid" is also referred to as "fats and oils" in some cases.

1. Acyl-ACP Thioesterase

The protein of the present invention includes a protein at least having an amino acid sequence of the $72^{nd}$ to $233^{rd}$ amino acids set forth in SEQ ID NO: 1, and a protein functionally equivalent to the protein. Specifically, the protein of the present invention includes the following proteins (a) to (c).

(a) A protein consisting of an amino acid sequence of the $72^{nd}$ to $233^{rd}$ amino acids set forth in SEQ ID NO: 1.
(b) A protein consisting of an amino acid sequence having 70% or more identity with the amino acid sequence of the protein (a), and having acyl-ACP thioesterase activity.
(c) A protein containing the amino acid sequence of the protein (a) or (b), and having acyl-ACP thioesterase activity.

The protein consisting of the amino acid sequence set forth in SEQ ID NO: 1 is a novel acyl-ACP thioesterase derived from an alga belonging to the genus *Symbiodinium*, *Symbiodinium microadriaticum*. *Symbiodinium microadriaticum* may be conventionally described and called with *Zooxanthella microadriatica* or *Gymnodinium microadriaticum*. Examples of *Symbiodinium microadriaticum* include *Symbiodinium microadriaticum* strain LB2281 (which is available from UTEX (The culture collection of algae at University of Texas at Austin)), and strains having the substantially same algological characteristics to *Symbiodinium microadriaticum* strain LB2281. Examples of the strains having the substantially same algological characteristics to *Symbiodinium microadriaticum* strain LB2281 include *Symbiodinium* sp. strain CCMP2948, *Symbiodinium* sp. strain CCMP2592, *Symbiodinium microadriaticum* strain CCMP827, and *Symbiodinium microadriaticum* strain CCMP2458.

The acyl-ACP (acyl carrier protein) thioesterase is an enzyme involved in the biosynthesis pathway of fatty acids and derivatives thereof (such as triacylglycerol (triglyceride)). This enzyme hydrolyzes a thioester bond of an acyl-ACP to form free fatty acids in a plastid such as a chloroplast of plants and algae or in a cytoplasm of bacteria, fungi and animals. The acyl-ACP is a composite composed of an acyl group as a fatty acid residue and an acyl carrier protein, and is an intermediate in the process of fatty acid biosynthesis. The function of the thioesterase terminates the synthesis of the fatty acid synthesis on the ACP, and then the thus-produced free fatty acids are supplied to the synthesis of triglyceride and the like. To date, several acyl-ACP thioesterases having different reaction specificities depending on the number of carbon atoms and the number of unsaturated bonds of acyl group (fatty acid residue) of acyl-ACP substrate are identified. Therefore, they are considered to be an important factor in determining fatty acid composition of an organism.

In the present invention, the "having acyl-ACP thioesterase activity" means having an activity of hydrolyzing a thioester bond of an acyl-ACP.

One example of nucleotide sequences encoding the amino acid sequence set forth in SEQ ID NO: 1 is a nucleotide sequence set forth in SEQ ID NO: 2. The gene consisting of the nucleotide sequence set forth in SEQ ID NO: 2 is a gene derived from *Symbiodinium microadriaticum*.

The present inventors have identified the gene consisting of the nucleotide sequence set forth in SEQ ID NO: 2 as an acyl-ACP thioesterase gene. Further, they have identified an important region for acyl-ACP thioesterase activity in the amino acid sequence encoded by the gene.

A recombinant protein at least having an amino acid sequence of the $72^{nd}$ to $233^{rd}$ amino acids set forth in SEQ ID NO: 1 acts as an acyl-ACP thioesterase as demonstrated in the working examples below. That is, it is thought that the region from $72^{nd}$ to $233^{rd}$ amino acids is sufficient for acyl-ACP thioesterase activity, with respect to the amino acid sequence set forth in SEQ ID NO: 1.

In the protein (b), the sequence identity of amino acid sequence is preferably 75% or more, more preferably 80% or more, further preferably 90% or more, further more preferably 95% or more, further more preferably 96% or more, further more preferably 97% or more, further more preferably 98% or more, and further more preferably 99% or more, in view of acyl-ACP thioesterase activity.

In the present specification, the sequence identity of the amino acid sequence and nucleotide sequence is calculated through the Lipman-Pearson method (see Science, 227, pp.1435, (1985)). Specifically, the identity can be determined through use of a homology analysis (homology search) program of genetic information processing software Genetyx-Win (Software Development Co., Ltd.) with the unit size to compare (ktup) being set to 2.

Preferred example of the protein (b) includes the following protein (b)'. (b)' A protein consisting of an amino acid sequence in which 1 or several amino acids (preferably 1 or more and 10 or less amino acids, more preferably 1 or more and 5 or less amino acids, and further preferably 1 or more and 3 or less amino acids) are mutated in the amino acid sequence of the protein (a), and having acyl-ACP thioesterase activity.

The above amino acid mutation includes deletion, substitution, addition or insertion of amino acid(s). A method of introducing the mutation into an amino acid sequence includes a method of, for example, introducing a mutation into a nucleotide sequence encoding the amino acid sequence. The method of introducing a mutation into a nucleotide sequence is described later.

The protein (c) is preferably a protein having the amino acid sequence of the protein (a). Moreover, the protein (c) is more preferably a protein consisting of an amino acid sequence set forth in SEQ ID NO: 1, a protein consisting of an amino acid sequence of the $32^{nd}$ to $233^{rd}$ amino acids set forth in SEQ ID NO: 1 and a protein consisting of an amino acid sequence of the $52^{nd}$ to $233^{rd}$ amino acids set forth in SEQ ID NO: 1. These proteins are confirmed to have the acyl-ACP thioesterase activity by Examples described later.

Moreover, the protein (c) also preferably includes a protein consisting of an amino acid sequence formed such that a signal peptide engaging in transport or secretion of the protein is added to the amino acid sequence of the protein (a) or (b). Specific examples of addition of the signal peptide include addition to an N terminus of chloroplast transit peptide.

The acyl-ACP thioesterase activity of the protein of the present invention can be measured by, for example, introducing a fusion gene produced by linking the acyl-ACP thioesterase gene to the downstream of a promoter which functions in a host cell such as *Escherichia coli*, into a host cell which lacks a fatty acid degradation system, culturing the thus-obtained cell under the conditions suitable for the expression of the introduced acyl-ACP thioesterase gene, and analyzing any change caused thereby in the fatty acid composition of the cell or the cultured liquid by using a gas chromatographic analysis or the like.

Alternatively, the acyl-ACP thioesterase activity can be measured by introducing a fusion gene produced by linking the acyl-ACP thioesterase gene to the downstream of a promoter which functions in a host cell such as *Escherichia coli*, into a host cell, culturing the thus-obtained cell under the conditions suitable for the expression of the introduced acyl-ACP thioesterase gene, and subjecting a disruption liquid of the cell to a reaction which uses acyl-ACPs, as substrates, prepared according to the method of Yuan et al. (Yuan L, Voelker T A, Hawkins D J. "Modification of the substrate specificity of an acyl-acyl carrier protein thioesterase by protein engineering", Proc. Natl. Acad. Sci. U.S.A., 1995 Nov. 7; 92 (23), p. 10639-10643).

There are no particular limitations on the method for obtaining the protein of the present invention, and the protein may be obtained by chemical techniques or genetic engineering techniques that are ordinarily carried out. For example, a natural product-derived protein can be obtained through isolation, purification and the like from *Symbiodinium microadriaticum*. Furthermore, the protein can also be artificially synthesized based on the information for the amino acid sequence set forth in SEQ ID NO: 1, and protein synthesis may be carried out by chemical synthesis, or a recombinant protein may also be produced by gene recombination technologies. In the case of producing a recombinant protein, the acyl-ACP thioesterase gene of the present invention described below can be used.

2. Acyl-ACP Thioesterase Gene

The gene of the present invention is a gene encoding any one of the proteins (a) to (c).

Specific examples of the gene encoding any one of the proteins (a) to (c) include a gene consisting of any one of DNAs (d) to (f) as follows:

(d) A DNA consisting of a nucleotide sequence of the $214^{th}$ to $699^{th}$ nucleotides set forth in SEQ ID NO: 2;

(e) A DNA consisting of a nucleotide sequence having 70% or more identity with the nucleotide sequence of the DNA (d), and encoding a protein having acyl-ACP thioesterase activity; and (f) A DNA containing the nucleotide sequence of the DNA (d) or (e), and encoding a protein having acyl-ACP thioesterase activity.

In the DNA (e) from the point of view of acyl-ACP thioesterase activity, the sequence identity of nucleotide sequence is preferably 75% or more, more preferably 80% or more, further preferably 90% or more, further more preferably 95% or more, further more preferably 96% or more, further more preferably 97% or more, further more preferably 98% or more, and further more preferably 99% or more. The sequence identity of nucleotide sequence can be calculated through the method described above.

Specific example of the DNA (e) is preferably the following DNA (e)': (e)' A DNA consisting of nucleotide sequence in which 1 or several nucleotides (preferably 1 or more and 10 or less nucleotides, more preferably 1 or more and 5 or less nucleotides, and further preferably 1 or more and 3 or less nucleotides) are mutated in the nucleotide sequence of the DNA (d), and having acyl-ACP thioesterase activity.

The above nucleotide mutation includes deletion, substitution, addition or insertion of nucleotide. A method of introducing the mutation into a nucleotide sequence includes a method of introducing a site-specific mutation. Specific examples of the method of introducing the site-specific mutation include a method of utilizing the Splicing overlap extension (SOE) PCR (Horton et al., Gene 77, 61-68, 1989), the ODA method (Hashimoto-Gotoh et al., Gene, 152, 271-276, 1995), and the Kunkel method (Kunkel, T. A., Proc. Natl. Acad. Sci. USA, 1985, 82, 488). Further, commercially available kits such as Site-Directed Mutagenesis System Mutan-SuperExpress Km kit (manufactured by Takara Bio), Transformer TM Site-Directed Mutagenesis kit (manufactured by Clonetech Laboratories), and KOD-Plus-Mutagenesis kit (manufactured by Toyobo) can also be utilized. Furthermore, a gene containing a desired mutation can also be obtained by introducing a genetic mutation at random, and then performing an evaluation of the enzyme activities and a gene analysis thereof by an appropriate method.

The DNA (f) is preferably a DNA having the nucleotide sequence of the DNA (d); and more preferably a DNA consisting of a nucleotide sequence set forth in SEQ ID NO: 2, a DNA consisting of a nucleotide sequence of the $94^{th}$ to $699^{th}$ nucleotides set forth in SEQ ID NO: 2, or a DNA consisting of a nucleotide sequence of the $154^{th}$ to $699^{th}$ nucleotides set forth in SEQ ID NO: 2. The proteins encoded by these DNAs are confirmed to have the acyl-ACP thioesterase activity by Examples described later.

Moreover, the DNA (f) also preferably includes a DNA consisting of a nucleotide sequence formed such that a nucleotide sequence encoding a signal peptide engaging in transport or secretion of the protein is added to the nucleotide sequence of the protein (d) or (e). Specific example of the signal peptide to be added thereto includes the proteins described in the protein (c).

A method of obtaining the acyl-ACP thioesterase gene of the present invention is not particularly limited, and the acyl-ACP thioesterase gene can be obtained by ordinary genetic engineering techniques. For example, the thioesterase gene of the present invention can be obtained by artificial synthesis based on the amino acid sequence set forth in SEQ ID NO: 1 or the nucleotide sequence set forth in SEQ ID NO: 2. The artificial synthesis of a gene can be achieved by utilizing the services of Invitrogen and the like. Furthermore, the gene can also be obtained by cloning from *Symbiodinium microadriaticum*. The cloning can be carried out by, for example, the methods described in Molecular Cloning—A LABORATORY MANUAL THIRD EDITION

[Joseph Sambrook, David W. Russell, Cold Spring Harbor Laboratory Press (2001)] and the like.

3. Transformant (1) First Embodiment

The transformant of the first embodiment of the present invention is obtained by introducing the acyl-ACP thioesterase gene of the present invention or a recombinant vector containing the gene into a host.

The introduction of the acyl-ACP thioesterase gene into a host can be carried out according to an ordinary genetic engineering method. Specifically, the transformant of the present invention can be produced by preparing an expression vector or gene expression cassette capable of expressing the acyl-ACP thioesterase gene of the present invention in a host cell, introducing it into a host cell to transform the host cell.

As the host cell used for the transformant, microorganisms, plants, animals and the like can be used. In the present invention, microorganisms include microalgae. Among these, microorganisms or plants are preferable, and microorganisms are more preferable, from the viewpoints of production efficiency of lipids and the usability of fatty acids.

As the microorganisms for the host cell, prokaryotes and eukaryotes can be used. Prokaryotes include microorganisms belonging to the genus *Escherichia* or microorganisms belonging to the genus *Bacillus*. Eukaryotes include eukaryotic microorganisms belonging to yeast or filamentous fungi. Among these, from the viewpoint of the productivity of lipids, *Escherichia coli, Bacillus subtilis, Rhodosporidium toruloides*, and *Mortierella* sp. are preferable, and *Escherichia coli* is more preferable.

As the microorganisms for the host cell, microalgae are also preferable. As the microalgae, from a viewpoint of establishment of a gene recombination technique, algae belonging to the genus *Chlamydomonas*, algae belonging to the genus *Chlorella*, algae belonging to the genus *Phaeodactylum*, algae belonging to the genus *Symbiodinium*, and algae belonging to the genus *Nannochloropsis* are preferable.

From the viewpoint of the productivity of lipids, algae belonging to the genus *Symbiodinium* and the genus *Nannochloropsis* are more preferable, and algae belonging to the genus *Nannochloropsis* are further preferable. Specific examples of the algae belonging to the genus *Symbiodinium* include *Symbiodinium microadriaticum, Symbiodinium goreaui, Symbiodinium linucheae, Symbiodinium bermudense, Symbiodinium meandrinae, Symbiodinium californium, Symbiodinium kawagutii, Symbiodinium corculorum, Symbiodinium consortia, Symbiodinium muscatinei, Symbiodinium freudenthal, Symbiodinium pulchrorum, and Symbiodinium pilosum*. Specific examples of the algae belonging to the genus *Nannochloropsis* include *Nannochloropsis oculata, Nannochloropsis paditana, Nannochloropsis salina, Nannochloropsis oceanica, Nannochloropsis atomus, Nannochloropsis maculata, Nannochloropsis granulata*, and *Nannochloropsis* sp. Among these, from the viewpoint of the productivity of lipids, *Nannochloropsis oculata* or *Nannochloropsis paditana* is preferable, and *Nannochloropsis oculata* is more preferable.

As the plants for the host cell, from the viewpoint of a lipid content of seeds, *Arabidopsis thaliana*, rapeseed, *Cocos nucifera*, palm, cuphea, and *Jatropha curcas* are preferable, and *Arabidopsis thaliana* is more preferable.

A vector for use as the expression vector may be any vector capable of introducing the acyl-ACP thioesterase gene of the present invention into a host cell, and expressing the gene in the host cell. For example, a vector which has expression regulation regions such as a promoter and a terminator in accordance with the type of the host cell to be used, and has a replication initiation point, a selection marker or the like, can be used. Furthermore, the vector may also be a vector capable of self-proliferation and self-replication outside the chromosome, such as a plasmid, or may also be a vector which is incorporated into the chromosome.

Specific examples of the vector include, in the case of using a microorganism as the host cell, pBluescript II SK(-) (manufactured by Stratagene), a pSTV-based vector (manufactured by Takara Bio), pUC-based vector such as pUC119 (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (Mckenzie, T. et al., (1986), Plasmid 15(2); p. 93-103), pBR322 (manufactured by Takara Bio), pRS403 (manufactured by Stratagene), and pMW218/219 (manufactured by Nippon Gene). In particular, in the case of using *Escherichia coli* as the host cell, pBluescript II SK(-) or pMW218/219 is preferably used.

When the algae are used as the host cell, specific examples of the vector include pUC19 (manufactured by Takara Bio), P66 (*Chlamydomonas* Center), P-322 (*Chlamydomonas* Center), pPha-T1 (see Non-Patent Literature 2 described above) and pJET1 (manufactured by COSMO B10). In particular, in the case of using the algae belonging to the genus *Nannochloropsis* as the host cell, pUC19 (manufactured by Takara Bio), pPha-T1 or pJET1 is preferably used. Moreover, when the host cell is the algae belonging to the genus *Nannochloropsis*, the host cell can be transformed, with referring to the method described in the literature, Oliver Kilian, et al., Proceedings of the National Academy of Sciences of the United States of America, December 27; 108(52), 2011, by using the DNA fragment consisting of the gene of the present invention, a promoter and a terminator (gene expression cassette). Specific examples of this DNA fragment include a PCR-amplified DNA fragment and a restriction enzyme-cut DNA fragment.

In the case of using a plant cell as the host cell, examples of the vector include a pRI-based vector (manufactured by Takara Bio), a pBI-based vector (manufactured by Clontech), and an IN3-based vector (manufactured by Inplanta Innovations). In particular, in the case of using *Arabidopsis thaliana* as the host cell, a pRI-based vector or a pBI-based vector is preferably used.

The expression regulation regions such as a promoter and a terminator, and the selection marker used for the expression vector and the gene expression cassette are not particularly limited, and can be appropriately selected from ordinarily used promoters, markers and the like in accordance with the type of the host cell to be used.

Specific examples of the promoter include lac promoter, trp promoter, tac promoter, trc promoter, T7 promoter, SpoVG promoter, cauliflower mosaic virus 35S RNA promoter, promoters for housekeeping genes such as tubulin promoter, actin promoter and ubiquitin promoter, rapeseed-derived Napin gene promoter, plant-derived Rubisco promoter, and a promoter of a violaxanthin/(chlorophyll a)-binding protein gene derived from the genus *Nannochloropsis*.

Examples of the selection marker include drug resistance genes such as antibiotic resistance genes (e.g. an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene). Further, it is also possible to use a deletion of an auxotrophy-related gene or the like as the selection marker gene.

The expression vector for transformation can be constructed by introducing the acyl-ACP thioesterase gene of the present invention into the above-described vector according to an ordinary technique such as restriction enzyme treatment and ligation.

The method for transformation is not particularly limited as long as it is a method capable of introducing a target gene into a host cell. For example, a method of using calcium ion, a general competent cell transformation method (J. Bacterial. 93, 1925 (1967)), a protoplast transformation method (Mol. Gen. Genet. 168, 111 (1979)), an electroporation method (FEMS Microbiol. Lett. 55, 135 (1990)), and an LP transformation method (T. Akamatsu and J. Sekiguchi, Archives of Microbiology, 1987, 146, p. 353-357; T. Akamatsu and H. Taguchi, Bioscience, Biotechnology, and Biochemistry, 2001, 65, 4, p. 823-829) and the like, can be used. When the host is the algae belonging to the genus *Nannochloropsis*, transformation can also be performed by applying the electroporation method described in Randor Radakovits, et al., Nature Communications, DOI: 10.1038/ncomms1688, 2012. When the host is the algae belonging to the genus *Symbiodinium*, transformation can also be performed by applying the SiC whisker method described in Michael R. ten Lohuis, David J. Miller, The Plant Journal, 1998, 13(3), p. 427-435.

The selection of a transformant having a target gene fragment introduced therein can be carried out by using the selection marker or the like. For example, the selection can be carried out by using an indicator whether a transformant acquires the drug resistance as a result of introducing a vector-derived drug resistance gene into a host cell together with a target DNA fragment. Further, the introduction of a target DNA fragment can also be confirmed by PCR using a genome as a template.

The transformant of the present embodiment can efficiently produce a fatty acid having a specific number of carbon atoms (chain length) and unsaturated bonds, and can produce improved amount of lipids. The ability to produce fatty acids of the transformant can be measured by the method used in Examples described below.

(2) Second Embodiment

The transformant of the second embodiment of the present invention is a transformant in which, in a host cell having the acyl-ACP thioesterase gene of the present invention, the gene is subjected to deletion, mutation or repression of gene expression. The transformant of the second embodiment can be obtained by deleting, mutating or repressing the acyl-ACP thioesterase gene of the present invention in the host cell.

The host cell of the transformant of this embodiment only needs to have the acyl-ACP thioesterase gene of the present invention. For example, microorganisms, plants or animals can be used as the host cell. Among these, microorganisms are preferable, and microalgae are more preferable, from the viewpoint of the productivity of lipids.

As the microalgae, from the viewpoint of the productivity of lipids, algae belonging to the genus *Symbiodinium* are preferable. Specific examples of the algae belonging to the genus *Symbiodinium* include *Symbiodinium microadriaticum*, *Symbiodinium goreaui*, *Symbiodinium linucheae*, *Symbiodinium bermudense*, *Symbiodinium meandrinae*, *Symbiodinium californium*, *Symbiodinium kawaqutii*, *Symbiodinium corculorum*, *Symbiodinium consortia*, *Symbiodinium muscatinei*, *Symbiodinium freudenthal*, *Symbiodinium pulchrorum*, and *Symbiodinium pilosum*. Among these, from the viewpoint of the productivity of lipids, *Symbiodinium microadriaticum* is more preferable.

The deletion, mutation or repression of the acyl-ACP thioesterase gene of the present invention from a host genome can be conducted by a method of partially or wholly removing a target gene from a genome, replacing the target gene by other genes, inserting other DNA fragments into the target gene, or providing mutation in an active site, a substrate-binding site, or a transcription or translation initiation region of the target gene.

The above method of deletion, mutation or repression of gene expression can employ, for example, homologous recombination techniques. Specifically, a linear DNA fragment containing an upstream and downstream regions of a target gene in a host genome but containing no target gene is constructed by a method such as PCR, and the resultant DNA fragment is incorporated into a host cell to cause double crossover homologous recombination on the side upstream and downstream of the target gene of the host genome, and then the target gene on the genome can be deleted or substituted for other gene fragment. Moreover, a target gene into which mutation such as nucleotide substitution and nucleotide insertion is introduced is constructed by a method such as PCR, and the resulting gene is incorporated into a host cell to cause double crossover homologous recombination in two regions outside the mutation site in the target gene of the host genome, and then a function of the target gene on the genome can be deteriorated or lost. Moreover, a cyclic recombinant plasmid is prepared by introducing a DNA fragment partially containing a target gene into a suitable plasmid vector, and the resultant plasmid is incorporated into a host cell to cause homologous recombination in part of region of the target gene on the host genome and to split the target gene of the host genome, and then a function of the target gene can be deteriorated or lost.

The method of deletion, mutation or repression of gene expression of a target gene using homologous recombination can be conducted with, for example, reference to literature such as Besher et al., Methods in molecular biology 47, pp. 291-302, 1995.

The selection of transformants with deletion or the like of the target gene can be made by a method of extracting genome DNA from the transformant and performing PCR to amplify a region containing the target gene, a southern blotting method using a DNA probe to be bonded with the target gene region, or the like.

With regard to the transformant of this embodiment, the acyl-ACP thioesterase gene of the present invention does not function. Therefore, the fatty acid composition of the lipid produced is considered to change from the composition original to the host. More specifically, the transformant can produce a lipid in which the fatty acid composition is modified.

4. Method of Producing Lipid

The transformant of the present invention is used for the production method of the present invention. The production method of the present invention contains culturing the transformant in medium, and collecting a lipid from the resulting cultured product. In the present invention, the culturing of a transformant includes culturing of a microorganism, algae, animal or plant, or a cell or tissue thereof, and also cultivating of a plant in soil or the like. Moreover, the cultured product includes medium used for culture, and a transformant subjected to cultivation or the like.

The medium and culture condition can be selected in accordance with the type of the host cell for transformation, and any appropriate preferred medium and condition can be employed. Further, from the viewpoint of an improvement in the productivity of lipids, substrates for thioesterase or precursor substances participating in the fatty acid biosynthesis, such as glycerol, acetic acid or malonic acid, may be added to the medium.

For instance, in the case of using *Escherichia coli* as the host cell for transformation, culture may be carried out in LB medium or Overnight Express Instant TB Medium (manufactured by Novagen) at 30° C. to 37° C. for half a day to 1 day. In the case of using *Arabidopsis thaliana* as the host cell for transformation, growth may be carried out under the temperature conditions of 20° C. to 25° C., by continuously irradiating white light or under white light illumination conditions of a light period of 16 hours and a dark period of 8 hours, for one to two months.

When the host cell of the transformation is the algae, the following culture media and culture conditions can be applied.

As the culture medium, medium based on natural seawater or artificial seawater may be used. Alternatively, commercially available culture medium may also be used. Specific examples of the culture medium include f/2 medium, ESM medium, Daigo IMK medium, L1 medium and MNK medium. Above all, from viewpoints of an improvement in the productivity of lipids and a nutritional ingredient concentration, f/2 medium, ESM medium or Daigo IMK medium is preferred; f/2 medium or Daigo IMK medium is more preferred; and f/2 medium is further preferred. For growth promotion of the algae and an improvement in productivity of a fatty acid, a nitrogen source, a phosphorus source, a metal salt, vitamins, a trace metal or the like can be appropriately added to the culture medium.

In view of viability, an amount of the algae to be inoculated to the culture medium is preferably 1% to 50% (vol/vol), and more preferably 1% to 10% (vol/vol), per culture medium. Culture temperature is not particularly limited within the range in which the temperature does not adversely affect growth of the algae, but is ordinarily in the range of 5° C. to 40° C. From viewpoints of the growth promotion of the algae, the improvement in productivity of a fatty acid, and reduction of production cost, the temperature is preferably 10° C. to 35° C., and more preferably 15° C. to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of a fatty acid, irradiance during the light irradiation is preferably in the range of 100 lx to 50,000 lx, more preferably in the range of 300 to 10,000 lx, and further preferably 1,000 lx to 6,000 lx. Moreover, from the viewpoints in a manner similar to the viewpoints described above, the irradiation is preferably performed under a light and dark cycle. In 24 hours, a light period is preferably 8 to 24 hours, more preferably 10 to 18 hours, and further preferably 12 hours.

Moreover, the algae are preferably cultured in the presence of a carbon dioxide-containing gas or in culture medium containing carbonate such as sodium hydrogen carbonate so that the photosynthesis can be made. From the viewpoints of the growth promotion or the improvement in the productivity of a fatty acid, a concentration of carbon dioxide in the gas is preferably 0.03% (which is the same degree as the concentration under atmospheric conditions) to 10%, more preferably 0.05% to 5%, further preferably 0.1% to 3%, and still further preferably 0.3% to 1%. When the sodium hydrogen carbonate is used, for example, from the viewpoints of the growth promotion and the improvement in the productivity of a fatty acid, a concentration of the carbonate is preferably 0.01% to 5% by mass, more preferably 0.05% to 2% by mass, and further preferably 0.1% to 1% by mass.

The culture may be performed for a long time (for example, about 150 days) so that an alga body in which the lipid is accumulated at a high concentration can grow at a high concentration. From the viewpoints of the growth promotion of the algae, the improvement in the productivity of a fatty acid, and the reduction of production cost, a culture time is preferably 3 to 90 days, more preferably 3 to 30 days, and further preferably 7 to 30 days. In addition, the culture may be performed in any of aerated and agitated culture, shaking culture or static culture. From a viewpoint of improving air-permeability, shaking culture is preferred.

Lipids produced in the transformant is isolated or collected by an ordinary method used for isolating lipid components and the like. For example, lipid components can be isolated and collected from the cultured product or transformant by means of filtration, centrifugation, cell disruption, gel filtration chromatography, ion exchange chromatography, chloroform/methanol extraction, hexane extraction, ethanol extraction, or the like. In the case of isolation and collection of larger scales, lipids can be obtained by collecting oil components from the cultured product or transformant through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The production method of the present invention can be preferably used in the production of fatty acids having 8 or more and 22 or less carbon atoms and derivatives thereof. Particularly, the production method of the present invention can be more preferably used in the production of fatty acids having 12 or more and 20 or less carbon atoms and derivatives thereof, further preferably used in the production of fatty acids having 12 or more and 16 or less carbon atoms and derivatives thereof, further more preferably used in the production of fatty acids having 12 or more and 14 or less carbon atoms and derivatives thereof, and particularly preferably used in the production of fatty acids having 12 or 14 carbon atoms and esters thereof.

The lipids obtained by the production method or the transformant of the present invention can be utilized for food, as well as can be utilized as an emulsifier incorporated into cosmetic products or the like, a cleansing agent such as a soap or a detergent, a fiber treatment agent, a hair conditioning agent, a disinfectant or an antiseptic. Moreover, the lipids can also be used as raw materials of biodiesel fuels.

With regard to the embodiments described above, the present invention also discloses a protein, a gene, a transformant, and a method described below.

<1> A protein selected from the group consisting of the following (a) to (c):
(a) A protein consisting of an amino acid sequence of the $72^{nd}$ to $233^{rd}$ amino acids set forth in SEQ ID NO: 1;
(b) A protein consisting of an amino acid sequence having 70% or more identity with the amino acid sequence of the protein (a), and having acyl-ACP thioesterase activity; and
(c) A protein containing the amino acid sequence of the protein (a) or (b), and having acyl-ACP thioesterase activity.

<2> The protein according to the above item <1>, wherein the identity of the protein (b) with the amino acid sequence of the protein (a) is 75% or more, preferably 80% or more, more preferably 90% or more, more preferably 95% or more, more preferably 96% or more, more preferably 97% or more, more preferably 98% or more, and more preferably 99% or more.

<3> The protein according to the above item <1>, wherein the protein (b) is a protein (b)' as follows:
(b)' A protein consisting of an amino acid sequence in which 1 or more and 10 or less amino acids, preferably 1 or more and 5 or less amino acids, and more preferably 1 or more and 3 or less amino acids, are deleted, substituted, added or inserted in the amino acid sequence of the protein (a), and having acyl-ACP thioesterase activity.

<4> The protein according to any one of the above items <1> to <3>, wherein the protein (c) is a protein consisting of an amino acid sequence set forth in SEQ ID NO: 1, a protein consisting of an amino acid sequence of the $32^{nd}$ to $233^{rd}$ amino acids set forth in SEQ ID NO: 1, or a protein consisting of an amino acid sequence of the $52^{nd}$ to $233^{rd}$ amino acids set forth in SEQ ID NO: 1.

<5> A gene encoding the protein according to any one of the above items <1> to <4>.

<6> A gene consisting of a DNA selected from the group consisting of the following (d) to (f):
(d) A DNA consisting of a nucleotide sequence of the $214^{th}$ to $699^{th}$ nucleotides set forth in SEQ ID NO: 2;
(e) A DNA consisting of a nucleotide sequence having 70% or more identity with the nucleotide sequence of the DNA (d), and encoding a protein having acyl-ACP thioesterase activity; and
(f) A DNA containing the nucleotide sequence of the DNA (d) or (e), and encoding a protein having acyl-ACP thioesterase activity.

<7> The gene according to the above item <6>, wherein the identity of the DNA (e) with the nucleotide sequence of the DNA (d) is 75% or more, preferably 80% or more, more preferably 90% or more, more preferably 95% or more, more preferably 96% or more, more preferably 97% or more, more preferably 98% or more, and more preferably 99% or more.

<8> A recombinant vector containing the gene according to any one of the above items <5> to <7>.

<9> A transformant obtained by introducing the gene according to any one of the above items <5> to <7> or the recombinant vector according to the above item <8> into a host.

<10> A transformant, wherein, in a host having the gene according to any one of the above items <5> to <7>, the gene is subjected to deletion, mutation or repression of gene expression.

<11> The transformant according to the above item <9> or <10>, wherein the host is a microorganism.

<12> The transformant according to the above item <11>, wherein the microorganism is a microalga.

<13> The transformant according to the above item <12>, wherein the microalga is an alga belonging to the genus *Chlamydomonas*, an alga belonging to the genus *Chlorella*, an alga belonging to the genus *Phaeodactylum*, an alga belonging to the genus *Symbiodinium*, or an alga belonging to the genus *Nannochloropsis*; preferably an alga belonging to the genus *Symbiodinium*, or an alga belonging to the genus *Nannochloropsis*; and more preferably an alga belonging to the genus *Nannochloropsis*.

<14> The transformant according to the above item <13>, wherein the alga belonging to the genus *Nannochloropsis* is *Nannochloropsis oculata, Nannochloropsis gaditana, Nannochloropsis salina, Nannochloropsis oceanica, Nannochloropsis atomus, Nannochloropsis maculata, Nannochloropsis qranulata*, or *Nannochloropsis* sp.; preferably *Nannochloropsis oculata* or *Nannochloropsis qaditana*; and more preferably *Nannochloropsis oculata*.

<15> The transformant according to the above item <13>, wherein the alga belonging to the genus *Symbiodinium* is *Symbiodinium microadriaticum, Symbiodinium poreaui, Symbiodinium linucheae, Symbiodinium bermudense, Symbiodinium meandrinae, Symbiodinium californium, Symbiodinium kawagutii, Symbiodinium corculorum, Symbiodinium consortia, Symbiodinium muscatinei, Symbiodinium freudenthal, Symbiodinium pulchrorum*, or *Symbiodinium pilosum*; preferably *Symbiodinium microadriaticum*.

<16> The transformant according to the above item <11>, wherein the microorganism is *Escherichia coli*.

<17> A method of producing a lipid, containing the steps of:
culturing the transformant according to any one of the above items <9> to <16> in medium; and collecting a lipid from the resulting cultured product.

<18> The method of producing a lipid according to the above item <17>, wherein the lipid contains fatty acids having 8 or more and 22 or less carbon atoms, preferably 12 or more and 20 or less carbon atoms, more preferably 12 or more and 16 or less carbon atoms, and further preferably 12 or more and 14 or less carbon atoms, and derivatives thereof.

<19> A method of modifying a fatty acid composition in a lipid, containing introducing the gene according to any one of the above items <5> to <7> into a host.

<20> A method of enhancing productivity of a lipid, containing introducing the gene according to any one of the above items <5> to <7> into a host.

<21> A method of modifying a fatty acid composition in a lipid, containing deleting, mutating or repressing the gene according to any one of the above items <5> to <7> in a host.

EXAMPLES

Hereinafter, the present invention will be described more in detail with reference to Examples, but the present invention is not limited thereto.

Example 1 Production of *Escherichia coli* Transformant Prepared by Introducing Acyl-ACP Thioesterases Gene Derived from *Symbiodinium*, and Production of Lipid by the Transformant 1. Preparation of the Acyl-ACP Thioesterases Gene Derived from *Symbiodinium*

As *Symbiodinium microadriaticum*, *Symbiodinium microadriaticum* strain LB2281 belonging to class Dinophyceae was obtained from The culture collection of algae at University of Texas at Austin (UTEX).

The total RNA of *Symbiodinium microadriaticum* strain LB2281 was extracted. The extracted total RNA was subjected to RNA sequencing using Roche Genome Sequencer FLX+system. Among the sequence obtained by the RNA sequencing, the gene designated as "contig26515" (gene consisting of the nucleotide sequence set forth in SEQ ID NO: 2) was subjected to identification of the function by the following method.

2. Construction of Plasmid for Contig26515 Gene Expression in *Escherichia coli*

The cDNA was obtained by reverse transcription using the total RNA of *Symbiodinium microadriaticum* strain LB2281 as a template, and Super Script™ III First-Strand Synthesis SuperMix for qRT-PCR (manufactured by invitrogen). PCR using a pair of primers set forth in SEQ ID NOS: 3 and 4 shown in Table 1 below and the above cDNA as a template, was carried out to prepare a gene fragment consisting of a nucleotide sequence of the $94^{th}$ to $699^{th}$ nucleotides set forth in SEQ ID NO: 2. Moreover, a plasmid vector pBluescriptII SK(−) (manufactured by Stratagene) was used as a template, and the pBluescriptII SK(−) was amplified by PCR using a pair of primers set forth in SEQ ID NOS: 5 and 6 shown in Table 1 below. Then, the resultant was subjected to digestion by restriction enzyme DpnI (manufactured by TOYOBO) treatment. These two fragments were purified using a High Pure PCR Product Purification Kit (manufactured by Roche Applied Science), and then fused using an In-Fusion HD Cloning Kit (manufactured by Clontech) to construct a plasmid contig26515_94 for contig26515 gene expression. This expression plasmid was constructed in the form of removing an amino acid sequence of the $1^{st}$ to $31^{st}$ amino acids on a side of an N-terminus of an amino acid sequence (SEQ ID NO: 1) encoded by the contig26515 gene, and fusing with an amino acid sequence of the $1^{st}$ to $29^{th}$ amino acids on a side of an N-terminus of a LacZ protein derived from the plasmid.

Using the cDNA of *Symbiodinium microadriaticum* strain LB2281 as a template, and a pair of any one of primers set forth in SEQ ID NOS: 7 and 8, and a primer set forth in SEQ ID NO: 4, shown in Table 1 below, PCR was carried out to prepare a gene fragment consisting of a nucleotide sequence of the $154^{th}$ to $699^{th}$ nucleotides set forth in SEQ ID NO: 2, and a gene fragment consisting of a nucleotide sequence of the $214^{th}$ to $699^{th}$ nucleotides set forth in SEQ ID NO: 2, respectively.

Each of the resultant gene fragments was fused with the pBluescriptII SK(−) vector in a manner similar to the method described above to construct a plasmid contig26515_154 for contig26515 gene expression and a plasmid contig26515_214 therefor, respectively. Herein, these expression plasmids were constructed in the form of removing amino acid sequences of the $1^{st}$ to $51^{st}$ amino acids and the $1^{st}$ to $71^{st}$ amino acids on the side of the N-terminus of the amino acid sequence (SEQ ID NO: 1) encoded by the contig26515 gene, respectively, and fusing with the amino acid sequence of the $1^{st}$ to $29^{th}$ amino acids on the side of the N-terminus of the LacZ protein derived from the plasmid.

TABLE 1

| | Nucleotide Sequence of Primers (5'→3') |
|---|---|
| SEQ ID NO: 3 | GCGGCCGCTCTAGAGTGCATCGCCATTACCGCTGGC |
| SEQ ID NO: 4 | ACAAAATATTAACGCTCACTTCTTTTTGACGATGTAC |
| SEQ ID NO: 5 | CTCTAGAGCGGCCGCCACCG |
| SEQ ID NO: 6 | GCGTTAATATTTTGTTAAAATTCG |
| SEQ ID NO: 7 | GCGGCCGCTCTAGAGGAGGGCATCTGGACTCCGCAC |
| SEQ ID NO: 8 | GCGGCCGCTCTAGAGATGGCGCTGAGAGACAGACAC |

3. Introduction of Contig26515 Gene Expression Plasmid into *Escherichia coli*

An *Escherichia coli* mutant strain, strain K27 (fadD88) (Overath et al, Eur. J. Biochem. 7, 559-574, 1969), was transformed by a competent cell transformation method, using each of the contig26515 gene expression plasmids constructed in the above. Each transformant was cultured overnight at 37° C., and each colony thus obtained was inoculated in 1 mL of LBAmp liquid medium (Bacto Trypton 1%, Yeast Extract 0.5%, NaCl 1%, and Ampicillin sodium 50 μg/mL), and then cultured overnight at 37° C. The culture fluid of 20 μL was inoculated to 2 mL of Overnight Express Instant TB Medium (Novagen) and was subjected to shaking culture at 30° C. After 16 hours cultivation, lipid components contained in the culture fluid were analyzed by the method described in the following item 4. As a negative control, *Escherichia coli* strain K27 transformed with the plasmid vector pBluescriptII SK(−) was also subjected to the same experiment.

4. Extraction of Lipid from *Escherichia coli* Culture Fluid and Analysis of Fatty Acids Contained Therein To 1 mL of the culture fluid, 504 of 7-pentadecanone (1 mg/mL) as an internal standard was added, and then 0.5 mL of chloroform, 1 mL of methanol and 10 μL of 2N hydrochloric acid were further added. The mixture was sufficiently stirred and then was left for 30 minutes. Further, 0.5 mL of chloroform and 0.5 mL of a 1.5% KCl were added thereto. The mixture was stirred and centrifuged for 15 minutes at 3,000 rpm, and then the chloroform layer (lower layer) was collected with pasteur pipette. A nitrogen gas was blown onto the resultant chloroform layer to be dried into solid, 0.7 mL of 0.5 N potassium hydroxide/methanol solution was added thereto, and the resultant mixture was kept warm at 80° C. for 30 minutes. One milliliter of 14% solution of boron trifluoride (manufactured by Sigma-Aldrich) was added to the sample, and the mixture was kept warm at 80° C. for 10 minutes. Thereafter, 1 mL of saturated saline and 1 mL of hexane were added thereto, and the mixture was vigorously stirred and then was left for 30 minutes at room temperature. Then, the hexane layer (upper layer) was collected to obtain fatty acid esters.

The obtain fatty acid esters were provided for gas chromatographic analysis. The gas chromatography analysis was carried out under the conditions as follows:
Capillary column: DB-1 MS 20 m×100 μm×0.10 μm (manufactured by J&W Scientific)
Mobile layer: high purity helium
Flow rate inside the column: 0.3 mL/min
Temperature rise program: 150° C. (for 0.5 min)→20° C./min→320° C. (for 2 min)
Equilibration time: for 1 min
Injection port: split injection (split ratio: 75:1)
Pressure 62.4 psi, 24.5 mL/min
Amount of injection 5 μL
Cleaning vial: methanol, chloroform
Detector temperature: 300° C.

Moreover, fatty acid ester was identified by providing the identical sample for a gas chromatography-mass spectrometry analysis under identical conditions.

Amounts of fatty acid methyl esters were quantitatively determined based on the peak areas of waveform data obtained by the above gas chromatographic analysis. The peak area corresponding to the each fatty acid methyl esters was compared with that of 7-pentadecanone as the internal standard, and carried out corrections between the samples, and then the amount of the each fatty acids per liter of the culture fluid was calculated. Further, the total amount of the each fatty acid was calculated by summing the amounts of the each fatty acids thus obtained, and ratio (weight percent) of the each fatty acid in the total amount of fatty acids was calculated.

Table 2 shows the results of measuring a ratio of each fatty acid and a total amount of fatty acids. Herein, in Table below, the description of "Cx:y" for the fatty acid composition represents a fatty acid having "x" as the number of carbon atoms, and "y" as the number of double bonds. Moreover, "TFA" presents a total amount of fatty acids, and "Fatty Acid Composition (% TFA)" presents a weight of each fatty acid relative to a weight of the total fatty acid.

Example 2 Production of Nannochloropsis Transformant Prepared by Introducing Acyl-ACP Thioesterase Gene Derived from Symbiodinium, and Production of Lipid by the Transformant 1. Construction of Plasmid for Contig26515 Gene Expression in Nannochloropsis Using the cDNA of *Symbiodinium microadriaticum* strain LB2281 as a template, and a pair of primers set forth in SEQ ID NOS: 9 and 10 shown in Table 3 below, PCR was carried out to prepare a contig26515 gene fragment consisting of a nucleotide sequence of the $154^{th}$ to $699^{th}$ nucleotides set forth in SEQ ID NO: 2.

A VCP1 promoter sequence (SEQ ID NO: 11), a VCP1 chloroplast transit signal sequence (SEQ ID NO: 12) and a VCP1 terminator sequence (SEQ ID NO: 13) were artificially synthesized based on the complete cds sequence (Accession number: JF957601.1) of the VCP1 (violaxanthin/(chlorophylla)-binding protein) gene of *Nannochloropsis* sp. strain W2J3B registered in GenBank. Using each of the thus-synthesized DNA fragments as a template, and a pair of primers set forth in SEQ ID NOS: 14 and 15, a pair of primers set forth in SEQ ID NOS: 16 and 17, and a pair of primers set forth in SEQ ID NOS: 18 and 19 as shown in Table 3 below, PCR was carried out to prepare the VCP1 promoter sequence, the VCP1 chloroplast transit signal sequence and the VCP1 terminator sequence, respectively. Moreover, using a plasmid vector pUC19 (manufactured by TAKARA B10) as a template, and a pair of primers set forth in SEQ ID NOS: 20 and 21 shown in Table 3 below, PCR was carried out to amplify the plasmid vector pUC19.

The contig26515 gene fragment, the VCP1 promoter sequence, the VCP1 chloroplast transit signal sequence and the VCP1 terminator sequence obtained as described above were fused with the plasmid vector pUC19 in a manner similar to the method in item 2. in Example 1 to construct an expression plasmid contig26515_154_Nanno for expression in *Nannochloropsis*. Herein, this expression plasmid consisted of the pUC19 vector sequence and an insert sequence (SEQ ID NO: 22; hereinafter, referred to as

TABLE 2

| Introduced plasmid | Total amount of fatty acids (mg/L) | Fatty Acid Composition (%) | | | | | | | | |
|---|---|---|---|---|---|---|---|---|---|---|
| | | C12:1 | C12:0 | C14:1 | C14:0 | C16:1 | C16:0 | C17:0 | C18:1 | C19:0 |
| pBluescriptII SK(−) | 182.0 | 0.0 | 0.0 | 0.0 | 6.2 | 2.2 | 50.1 | 28.5 | 5.8 | 7.3 |
| contig26515_94 | 581.9 | 11.5 | 6.0 | 16.0 | 12.6 | 22.1 | 18.2 | 6.0 | 5.9 | 1.6 |
| contig26515_154 | 431.1 | 16.2 | 6.1 | 18.3 | 13.2 | 24.4 | 12.8 | 5.5 | 3.1 | 0.6 |
| contig26515_214 | 468.5 | 5.9 | 5.8 | 8.9 | 15.9 | 15.2 | 28.6 | 10.1 | 7.1 | 2.4 |

As shown in Table 2, an increase in a total amount of fatty acids was observed in the transformants having the contig26515 gene fragment in comparison with the transformant having the plasmid vector pBluescriptII SK(−). Moreover, the fatty acid composition changed in the transformants in comparison with the transformant having the plasmid vector pBluescriptII SK(−). In particular, ratios of the fatty acids of C12:1, C12:0, C14:1, C14:0 and C16:1 increased. From these results, the protein encoded by the contig26515 gene is thought to be the acyl-ACP thioesterase cutting out a specific fatty acid from acyl-ACP. Moreover, a protein containing at least the amino acid sequence of the $72^{nd}$ to $233^{rd}$ amino acids set forth in SEQ ID NO: 1 was found to have the acyl-ACP thioesterase activity.

"fragment for contig26515 gene expression") in which the VCP1 promoter sequence, the VCP1 chloroplast transit signal sequence, the contig26515 gene fragment and the VCP1 terminator sequence were linked in this order.

2. Construction of Plasmid for Zeocin Resistance Gene Expression in Nannochloropsis A Zeocin resistance gene (SEQ ID NO: 23), and a tubulin promoter sequence (SEQ ID NO: 24) derived from *Nannochloropsis paditana* strain CCMP526 described in Randor Radakovits, et al., Nature Communications, DOI:10.1038/ncomms1688, 2012 were artificially synthesized. Using each of the thus-synthesized DNA fragments as a template, and a pair of primers set forth in SEQ ID NOS: 25 and 26, and a pair of primers set forth in SEQ ID NOS: 27 and 28, PCR was carried out to prepare a Zeocin resistance gene and a tubulin promoter sequence, respectively. These amplified fragments, and the amplified fragments of the VCP1 terminator and a plasmid vector pUC19 prepared in item 1. were fused as described above in a manner similar to the method in item 2. in Example 1 to construct a Zeocin resistance gene expression plasmid. Herein, this expression plasmid consisted of a pUC19 vector sequence, and an insert sequence (SEQ ID NO: 29; hereinafter, referred to as "fragment for Zeocin resistance gene expression") in which the tubulin promoter sequence, the Zeocin resistance gene, and the VCP1 terminator sequence were linked in this order.

3. Introduction of Fragment for Contig26515 Gene Expression into *Nannochloropsis*

Using the expression plasmid contig26515_154_Nanno as a template, and a pair of primers set forth in SEQ ID NOS: 30 and 31 shown in Table 3 below, PCR was carried out to amplify a fragment for contig26515 gene expression (SEQ ID NO: 22) in the plasmid. Moreover, using the plasmid for Zeocin resistance gene expression as a template, and a pair of primers set forth in SEQ ID NOS: 31 and 32, PCR was carried out to amplify a fragment for Zeocin resistance gene expression (SEQ ID NO: 29). Both of the amplified fragments were purified using a High Pure PCR Product Purification Kit (manufactured by Roche Applied Science). Herein, sterilized water was used for elution upon purification without using an elution buffer included in the kit.

About $10^9$ cells of *Nannochloropsis oculata* strain NIES2145 were washed with 384 mM sorbitol solution to completely remove a salt, and the resultant was used as a host cell of transformation. The amplified fragment for contig26515 gene expression (SEQ ID NO: 22) and fragment for Zeocin resistance gene expression (SEQ ID NO: 29) as described above were mixed by about 500 ng for each with the host cell, and electroporation was carried out under conditions of 50 μF, 500Ω and 2,200 v/2 mm. After 24 hours recovery cultivation in f/2 liquid medium (75 mg $NaNO_3$, 6 mg $NaH_2PO_4.2H_2O$, 0.5 μg vitamin B12, 0.5 μg biotin, 100 μg thiamine, 10 mg $Na_2SiO_3.9H_2O$, 4.4 mg $Na_2EDTA.2H_2O$, 3.16 mg$FeCl_3.6H_2O$, 12 μg $FeCl_3.6H_2O$, 21 μg $ZnSO_4.7H_2O$, 180 μg$MnCl_2.4H_2O$, 7 μg $CuSO_4.5H_2O$, 7 μg $Na_2MoO_4.2H_2O$/artificial sea water 1 L), the resultant material was inoculated in f/2 agar medium containing 2 μg/mL of Zeocin, and cultured for two to three weeks under 12 h/12 h light-dark conditions at 25° C. under an atmosphere of 0.3% $CO_2$. A transformant containing the fragment for contig26515 gene expression (SEQ ID NO: 22) was selected from the resultant colonies by a PCR method. The thus-selected strain was inoculated to 20 mL of culture medium (hereinafter, referred to as "N15P5 medium") in which a nitrogen concentration in the f/2 medium was reinforced 15 times, and a phosphorus concentration therein was reinforced 5 times, and subjected to shaking culture for four weeks under the 12 h/12 h light-dark conditions at 25° C. under the atmosphere of 0.3% $CO_2$ (preculture fluid). Then, 2 mL of the preculture fluid was inoculated to 18 mL of the N15P5 medium, and subjected to shaking culture for two weeks under the 12 h/12 h light-dark conditions at 25° C. under the atmosphere of 0.3% $CO_2$. In addition, as a negative control, an experiment was also conducted on the wild type strain NIES2145.

TABLE 3

| | Nucleotide Sequence of Primers (5'→3') |
|---|---|
| SEQ ID NO: 9 | CGCGGTGTTGCGCGCGAGGGCATCTGGACTCCGCAC |
| SEQ ID NO: 10 | CTCTTCCACAGAAGCTCACTTCTTTTTGACGATGTAC |
| SEQ ID NO: 14 | CGAGCTCGGTACCCGGGCGGTCTTTTGTCCTTTCCTC |
| SEQ ID NO: 15 | AATCTGCTCGGAGGGGAGGATC |
| SEQ ID NO: 16 | CCCTCCGAGCAGATTATGAAGACCGCCGCTCTCCTC |
| SEQ ID NO: 17 | GCGCGCAACACCGCGGGTGCGGGAGAAC |
| SEQ ID NO: 18 | GCTTCTGTGGAAGAGCCAGTG |
| SEQ ID NO: 19 | ACTCTAGAGGATCCCCTGATCTTGTCCATCTCGTG |
| SEQ ID NO: 20 | GGGATCCTCTAGAGTCGACC |
| SEQ ID NO: 21 | CGGGTACCGAGCTCGAATTC |
| SEQ ID NO: 25 | CTTTTTTGTGAAGCAATGGCCAAGTTGACCAGTGCCG |
| SEQ ID NO: 26 | CTCTTCCACAGAAGCTTAGTCCTGCTCCTCGGCCACG |
| SEQ ID NO: 27 | CGAGCTCGGTACCCGACTGCGCATGGATTGACCGA |
| SEQ ID NO: 28 | TGCTTCACAAAAAAGACAGCTTCTTGAT |
| SEQ ID NO: 30 | GGCGGTCTTTTGTCCTTTCCTC |
| SEQ ID NO: 31 | CTGATCTTGTCCATCTCGTG |
| SEQ ID NO: 32 | ACTGCGCATGGATTGACCGA |

4. Extraction of Lipid from *Nannochloropsis* Culture Fluid, and Analysis of Fatty Acids Contained Therein The extraction of lipid from the resultant *Nannochloropsis* culture fluid and the analysis of the constituent fatty acid were carried out in a manner similar to the method in item 4. in Example 1.

Table 4 shows the results. Herein, in Table 4 below, the description of "Cx:y" for the fatty acid composition represents a fatty acid having "x" as the number of carbon atoms, and "y" as the number of double bonds. In addition, "n" represents an integer of 0 to 5. For example, when "C18:n" was described, the description represents a total of fatty acids having compositions of C18:0, C18:1, C18:2, C18:3, C18:4 and C18:5.

TABLE 4

| | Total amount of fatty acids | Fatty Acid Composition (% TFA) | | | | | |
|---|---|---|---|---|---|---|---|
| | (mg/L) | C12:0 | C14:0 | C16:1 | C16:0 | C18:n | C20:n |
| NIES2145 | 270.6 ± 25.4 | 0.0 ± 0.0 | 4.3 ± 0.1 | 26.4 ± 0.9 | 28.9 ± 2.4 | 11.8 ± 1.3 | 28.6 ± 4.4 |
| contig26515_154_Nanno | 367.7 ± 59.0 | 2.9 ± 0.3 | 6.6 ± 0.3 | 36.3 ± 0.7 | 20.2 ± 2.3 | 10.7 ± 1.0 | 23.4 ± 3.9 |

As shown in Table 4, in the *Nannochloropsis* transformant having the contig26515 gene fragment, an increase in a total amount of fatty acid was observed in comparison with the *Nannochloropsis* strain NIES2145. Moreover, the fatty acid composition changed in the transformant in comparison with the *Nannochloropsis* strain NIES2145. In particular, ratios of the fatty acids of C12:0, C14:0 and C16:1 increased.

Example 3 Production of *Escherichia coli* Transformant Prepared by Introducing Acyl-ACP Thioesterase Variant Derived from *Symbiodinium*, and Production of Lipid by the Transformant 1. Construction of Plasmid for Acyl-ACP Thioesterase Variant Expression Derived from *Symbiodinium*

As a nucleotide sequences encoding the protein set forth in SEQ ID NO: 33, a gene consisting of a nucleotide sequence set forth in SEQ ID NO: 34 was prepared by synthesis of an artificial gene. Herein, the amino acid sequence set forth in SEQ ID NO: 33 has about 75% identity with the amino acid sequence of the $72^{nd}$ to $233^{rd}$ amino acids set forth in SEQ ID NO: 1.

A gene fragment consisting of a nucleotide sequence set forth in SEQ ID NO: 34 was amplified by PCR using a pair of primers set forth in SEQ ID NOS: 35 and 36 shown in Table 5 below and the artificial gene above as a template. The resultant gene fragment was subjected in a manner similar to the method in item 2. in Example 1 to construct an expression plasmid Symbio317. Herein, this expression plasmids was constructed in the form of removing the $1^{st}$ amino acid on the side of the N-terminus of the amino acid sequence set forth in SEQ ID NO: 33, and fusing with the amino acid sequence of the $1^{st}$ to $29^{th}$ amino acids on the side of the N-terminus of the LacZ protein derived from the plasmid.

TABLE 5

| | Nucleotide Sequence of Primers (5'→3') |
|---|---|
| SEQ ID NO: 35 | GCGGCCGCTCTAGAGAACGAGCGGAGGGAGGAGATAC |
| SEQ ID NO: 36 | ACAAAATATTAACGCGTCGTCATAGATTGCAGCGTTTAG |

2. Introduction of Expression Plasmid into *Escherichia coli*, Extraction of Lipid from *Escherichia coli* Culture Fluid, and Analysis of Fatty Acids Contained Therein The expression plasmid Symbio317 was introduced into *Escherichia coli* in a manner similar to the method in item 3. in Example 1 to analyze a lipid in a manner similar to the method in item 4. in Example 1'. Table 6 shows the results.

TABLE 6

| | TFA | Fatty Acid Composition (% TFA) | | | | | | | | |
|---|---|---|---|---|---|---|---|---|---|---|
| | (mg/L) | C12:1 | C12:0 | C14:1 | C14:0 | C16:1 | C16:0 | C17:0 | C18:1 | C19:0 |
| pBluescriptII SK(−) | 192.7 | 0.0 | 1.2 | 0.0 | 7.7 | 2.3 | 47.3 | 27.5 | 6.1 | 7.9 |
| Symbio317 | 335.5 | 1.5 | 4.6 | 5.4 | 19.1 | 9.8 | 32.6 | 14.3 | 8.6 | 4.1 |

As shown in Table 6, an increase in a total amount of fatty acids was observed in the transformant having the expression plasmid Symbio317 in comparison with the transformant having the plasmid vector pBluescriptII SK(−). Moreover, the fatty acid composition changed in the transformant in comparison with the transformant having the plasmid vector pBluescriptII SK(−). In particular, ratios of the fatty acids of C12:1, C12:0, C14:1, C14:0 and C16:1 increased. From these results, the protein set forth in SEQ ID NO: 33 was found to have the acyl-ACP thioesterase activity.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2013-146624 filed in Japan on Jul. 12, 2013, which is entirely herein incorporated by reference.

What is claimed is:

1. A method of producing a lipid, comprising the steps of:
culturing a transformant in a culture medium under conditions suitable for production of lipid to produce a cultured product, and
collecting the lipid from the resulting cultured product,
wherein the transformant is a host organism transformed with a heterologous gene encoding a protein selected from the group consisting of the following (a) to (c), wherein the host organism is a microorganism or a plant cell:
(a) A protein consisting of the amino acid sequence of:
the 72nd to 233rd amino acids set forth in SEQ ID NO: 1;
the amino acid sequence set forth in SEQ ID NO: 33: or
the 2nd to 167th amino acids set forth in SEQ ID NO: 33,
(b) A protein having acyl-ACP thioesterase activity and consisting of an amino acid sequence with 90% or more sequence identity to the amino acid sequence of the protein of (a); and
(c) A protein comprising the amino acid sequence of the protein of (a) or (b), and having acyl-ACP thioesterase activity.

2. The method of producing a lipid according to claim 1 wherein the protein is protein (c) and protein (c) is
a protein consisting of the amino acid sequence set forth in SEQ ID NO: 1,
a protein consisting of the amino acid sequence of the 32nd to 233rd amino acids set forth in SEQ ID NO: 1,
a protein consisting of the amino acid sequence of the 52nd to 233rd amino acids set forth in SEQ ID NO: 1,
a protein consisting of the amino acid sequence set forth in SEQ ID NO: 33, or
a protein consisting of the amino acid sequence of the 2nd to 167th amino acids set forth in SEQ ID NO: 33.

3. The method of producing a lipid according to claim 1, wherein the lipid comprises fatty acids having 12 or more and 14 or less carbon atoms.

4. The method of producing a lipid according to claim 1 wherein the protein is encoded by a DNA selected from the group consisting of the following (d) to (j):
(d) A DNA consisting of the nucleotide sequence of the 214th to 699th nucleotides set forth in SEQ ID NO: 2;
(e) A DNA consisting of the nucleotide sequence set forth in SEQ ID NO: 2;
(f) A DNA consisting of the nucleotide sequence of the 94th to 699th nucleotides set forth in SEQ ID NO: 2;
(g) A DNA consisting of the nucleotide sequence of the 154th to 699th nucleotides set forth in SEQ ID NO: 2;
(h) A DNA consisting of the nucleotide sequence set forth in SEQ ID NO: 34;
(i) A DNA encoding a protein having acyl-ACP thioesterase activity and consisting of a nucleotide sequence with 90% or more sequence identity to the nucleotide sequence of a DNA selected from the group consisting of the DNAs of (d) to (g); and
(j) A DNA comprising the nucleotide sequence of a DNA selected from the group consisting of the DNAs of (d) to (i), and encoding a protein having acyl-ACP thioesterase activity.

5. The method of producing a lipid according to claim 1 wherein the host organism is a microorganism.

6. A method of modifying the fatty acid composition of a lipid, comprising (i) transforming a host organism with a gene encoding a protein selected from the group consisting of the following (a) to (c), wherein the host organism is a microorganism or a plant cell:
  (a) A protein consisting of the amino acid sequence of:
    the 72nd to 233rd amino acids set forth in SEQ ID NO: 1;
    the amino acid sequence set forth in SEQ ID NO: 33; or
    the 2nd to 167th amino acids set forth in SEQ ID NO: 33;
  (b) A protein having acyl-ACP thioesterase activity and consisting of an amino acid sequence with 90% or more sequence identity to the amino acid sequence of the protein of (a); and
  (c) A protein comprising the amino acid sequence of the protein of (a) or (b), and having acyl-ACP thioesterase activity,
(ii) culturing the transformed host organism of part (i) in a culture medium;
(iii) expressing the protein encoded by the gene in the transformed host organism; and
(iv) collecting lipid produced by the transformed host organism during the culturing from the transformed host organism or from the culture medium;
wherein the fatty acid composition of the lipid that is collected in part (iv) is modified, as compared to that of a control host organism that is not transformed with the gene.

7. The method of modifying the fatty acid composition of a lipid according to claim 6 wherein the protein is protein (c) and protein (c) is
  a protein consisting of the amino acid sequence set forth in SEQ ID NO: 1,
  a protein consisting of the amino acid sequence of the 32nd to 233rd amino acids set forth in SEQ ID NO: 1,
  a protein consisting of the amino acid sequence of the 52nd to 233rd amino acids set forth in SEQ ID NO: 1,
  a protein consisting of the amino acid sequence set forth in SEQ ID NO: 33, or
  a protein consisting of the amino acid sequence of the 2nd to 167th amino acids set forth in SEQ ID NO: 33.

8. The method of modifying the fatty acid composition of a lipid according to claim 6 wherein the protein is encoded by a DNA selected from the group consisting of the following (d) to (j):
  (d) A DNA consisting of the nucleotide sequence of the 214th to 699th nucleotides set forth in SEQ ID NO: 2;
  (e) A DNA consisting of the nucleotide sequence set forth in SEQ ID NO: 2;
  (f) A DNA consisting of the nucleotide sequence of the 94th to 699th nucleotides set forth in SEQ ID NO: 2;
  (g) A DNA consisting of the nucleotide sequence of the 154th to 699th nucleotides set forth in SEQ ID NO: 2;
  (h) A DNA consisting of the nucleotide sequence set forth in SEQ ID NO: 34;
  (i) A DNA encoding a protein having acyl-ACP thioesterase activity and consisting of a nucleotide sequence with 90% or more sequence identity to the nucleotide sequence of a DNA selected from the group consisting of the DNAs of (d) to (g); and
  (j) A DNA comprising the nucleotide sequence of a DNA selected from the group consisting of the DNAs of (d) to (i), and encoding a protein having acyl-ACP thioesterase activity.

9. The method of modifying the fatty acid composition of a lipid according to claim 6 wherein the host organism is a microorganism.

10. A method of enhancing productivity of a lipid, comprising
(i) transforming a host organism with a gene encoding a protein selected from the group consisting of the following (a) to (c), wherein the host organism is a microorganism or a plant cell:
  (a) A protein consisting of the amino acid sequence of:
    the 72nd to 233rd amino acids set forth in SEQ ID NO: 1;
    the amino acid sequence set forth in SEQ ID NO: 33; or
    the 2nd to 167th amino acids set forth in SEQ ID NO: 33;
  (b) A protein having acyl-ACP thioesterase activity and consisting of an amino acid sequence with 90% or more sequence identity to the amino acid sequence of the protein of (a); and
  (c) A protein comprising the amino acid sequence of the protein of (a) or (b), and having acyl-ACP thioesterase activity,
(ii) culturing the transformed host organism of part (i) in a culture medium;
(iii) expressing the protein encoded by the gene in the transformed host organism; and
(iv) collecting lipid produced by the transformed host organism during the culturing from the transformed host organism or from the culture medium;
wherein production of the lipid that is collected in part (iv) is increased, as compared to that of a control host organism that is not transformed with the gene.

11. The method of enhancing productivity of a lipid according to claim 10 wherein the protein is protein (c) and protein (c) is
  a protein consisting of the amino acid sequence set forth in SEQ ID NO: 1,
  a protein consisting of the amino acid sequence of the 32nd to 233rd amino acids set forth in SEQ ID NO: 1,
  a protein consisting of the amino acid sequence of the 52nd to 233rd amino acids set forth in SEQ ID NO: 1,
  a protein consisting of the amino acid sequence set forth in SEQ ID NO: 33, or
  a protein consisting of the amino acid sequence of the 2nd to 167th amino acids set forth in SEQ ID NO: 33.

12. The method of enhancing productivity of a lipid according to claim 10 wherein the lipid comprises fatty acids having 12 or more and 14 or less carbon atoms.

13. The method of enhancing productivity of a lipid according to claim 10 wherein the protein is encoded by a DNA selected from the group consisting of the following (d) to (j):
  (d) A DNA consisting of the nucleotide sequence of the 214th to 699th nucleotides set forth in SEQ ID NO: 2;
  (e) A DNA consisting of the nucleotide sequence set forth in SEQ ID NO: 2;
  (f) A DNA consisting of the nucleotide sequence of the 94th to 699th nucleotides set forth in SEQ ID NO: 2;
  (g) A DNA consisting of the nucleotide sequence of the 154th to 699th nucleotides set forth in SEQ ID NO: 2;
  (h) A DNA consisting of the nucleotide sequence set forth in SEQ ID NO: 34;
  (i) A DNA encoding a protein having acyl-ACP thioesterase activity and consisting of a nucleotide sequence with 90% or more sequence identity to the nucleotide sequence of a DNA selected from the group consisting of the DNAs of (d) to (g); and (j) A DNA comprising the nucleotide sequence of a DNA selected from the group consisting of the DNAs of (d) to (i), and encoding a protein having acyl-ACP thioesterase activity.

14. The method of producing a lipid according to claim 1 wherein the host organism is a microorganism.

15. A transformant transformed with a heterologous gene encoding a protein selected from the group consisting of the following (a) to (c), or a recombinant vector comprising the gene, wherein the transformant is a microorganism or an isolated plant cell:

(a) A protein consisting of the amino acid sequence of:
the 72nd to 233rd amino acids set forth in SEQ ID NO: 1;
the amino acid sequence set forth in SEQ ID NO: 33: or
the 2nd to 167th amino acids set forth in SEQ ID NO: 33, (b) A protein having acyl-ACP thioesterase activity and consisting of an amino acid sequence with 90% or more sequence identity to the amino acid sequence of the protein of (a); and (c) A protein comprising the amino acid sequence of the protein of (a) or (b), and having acyl-ACP thioesterase activity.

16. The transformant according to claim 15 wherein the protein is protein (c) and protein (c) is
a protein consisting of the amino acid sequence set forth in SEQ ID NO: 1,
a protein consisting of the amino acid sequence of the 32nd to 233rd amino acids set forth in SEQ ID NO: 1,
a protein consisting of the amino acid sequence of the 52nd to 233rd amino acids set forth in SEQ ID NO: 1,
a protein consisting of the amino acid sequence set forth in SEQ ID NO: 33, or
a protein consisting of the amino acid sequence of the 2nd to 167th amino acids set forth in SEQ ID NO: 33.

17. The transformant according to claim 15 wherein the protein is encoded by a DNA selected from the group consisting of the following (d) to (j):

(d) A DNA consisting of the nucleotide sequence of the 214th to 699th nucleotides set forth in SEQ ID NO: 2;

(e) A DNA consisting of the nucleotide sequence set forth in SEQ ID NO: 2;

(f) A DNA consisting of the nucleotide sequence of the 94th to 699th nucleotides set forth in SEQ ID NO: 2;

(g) A DNA consisting of the nucleotide sequence of the 154th to 699th nucleotides set forth in SEQ ID NO: 2;

(h) A DNA consisting of the nucleotide sequence set forth in SEQ ID NO: 34;

(i) A DNA encoding a protein having acyl-ACP thioesterase activity and consisting of a nucleotide sequence with 90% or more sequence identity to the nucleotide sequence of a DNA selected from the group consisting of the DNAs of (d) to (g); and (j) A DNA comprising the nucleotide sequence of a DNA selected from the group consisting of the DNAs of (d) to (i), and encoding a protein having acyl-ACP thioesterase activity.

18. The transformant according to claim 15 wherein the transformant is a microorganism.

* * * * *

SEQUENCE LISTING

<160> NUMBER OF SEQ ID NOS: 36

<210> SEQ ID NO 1
<211> LENGTH: 233
<212> TYPE: PRT
<213> ORGANISM: Symbiodinium microadriaticum

<400> SEQUENCE: 1

Met Ala Phe Arg Leu Cys Ser Leu Ser Arg Arg Phe Ala Ala His Ala
1               5                   10                  15

Gln Gln Val Leu Arg Lys Glu Ala Gly Phe Glu Phe Arg Ala Ser Cys
            20                  25                  30

Ile Ala Ile Thr Ala Gly Ile Ser Ala Gly Trp Cys Met Gln Gln Ala
        35                  40                  45

Ala Arg Ala Glu Gly Ile Trp Thr Pro His Leu Gly Glu Glu Ala Lys
    50                  55                  60

Leu Leu Asn Leu Gln Arg Glu Met Ala Leu Arg Asp Arg His Asp Lys
65                  70                  75                  80

Gln Phe Val Trp Gln Thr Cys Ser Gly Gln Gly Lys Ile Glu Asp Cys
                85                  90                  95

Arg Ile Tyr His Cys Lys Arg Glu Glu Val Asp Arg Glu Val Ser Leu
            100                 105                 110

Asp Ala Pro Glu Met Val Glu Gly Lys Thr Arg Ile Cys Ala Val Met
        115                 120                 125

Arg Val Gly Asp Glu Leu Asn Gly His Pro Gly Leu Leu His Gly Gly
    130                 135                 140

Phe Thr Ala Ala Val Leu Asp Asp Phe Thr Gly Leu Ala Thr Trp Met
145                 150                 155                 160

Glu Lys Gln Ala Gln Ala Leu Asp Lys Asp Ala Ala Ile Phe Thr Ala
                165                 170                 175

His Met Asp Leu Ser Tyr Arg Arg Pro Leu Lys Ala Lys Ser Glu Tyr
            180                 185                 190

Leu Val Glu Val Cys Val Asp Arg Val Glu Arg Gln Lys Lys Val Phe
        195                 200                 205

Leu Asn Ala Ala Ile Tyr Asp Lys Asp Ser His Ala Cys Val Lys Ala
    210                 215                 220

Lys Val Leu Tyr Ile Val Lys Lys Lys
225                 230

<210> SEQ ID NO 2
<211> LENGTH: 702
<212> TYPE: DNA
<213> ORGANISM: Symbiodinium microadriaticum

<400> SEQUENCE: 2
atggctttca ggctatgctc tctttcccgg cggtttgctg cgcacgcgca gcaggtgctg      60
cggaaggagg ctggctttga gttccgcgca agctgcatcg ccattaccgc tggcatctct     120
gctggatggt gcatgcagca ggcagcgcgg gcggagggca tctggactcc gcacctgggc     180
gaggaggcca agttgttgaa cctccagcgc gagatggcgc tgagagacag acacgacaag     240
caatttgtgt ggcagacctg cagtggccag ggcaaaattg aggactgccg catatatcac     300
tgcaagcgag aagaagttga tcgtgaggtt cgctggacg cgccggaaat ggtggagggc      360
aaaacacgga tttgtgcagt gatgcgcgtt ggcgacgagc tgaacggcca tcctgggctt     420
ttgcatggcg gcttcactgc cgccgtgctg gacgatttca caggcctggc gacctggatg     480

```
gagaagcaag cgcaggcgct ggacaaggat gcggccattt tcaccgctca catggatctc      540
agctatcggc gaccccctgaa ggcgaagtcg gagtacttgg ttgaggtttg cgttgaccgt     600
gttgagcggc aaaagaaggt ctttctgaat gctgccatct atgacaagga cagccatgcc     660
tgcgtgaaag caaaggtgtt gtacatcgtc aaaaagaagt ga                        702
```

```
<210> SEQ ID NO 3
<211> LENGTH: 36
<212> TYPE: DNA
<213> ORGANISM: Artificial Sequence
<220> FEATURE:
<223> OTHER INFORMATION: PCR primer 1 for thioesterase

<400> SEQUENCE: 3
gcggccgctc tagagtgcat cgccattacc gctggc                                36

<210> SEQ ID NO 4
<211> LENGTH: 37
<212> TYPE: DNA
<213> ORGANISM: Artificial Sequence
<220> FEATURE:
<223> OTHER INFORMATION: PCR primer 2 for thioesterase

<400> SEQUENCE: 4
acaaaatatt aacgctcact tcttttttgac gatgtac                              37

<210> SEQ ID NO 5
<211> LENGTH: 20
<212> TYPE: DNA
<213> ORGANISM: Artificial Sequence
<220> FEATURE:
<223> OTHER INFORMATION: PCR primer 1 for plasmid

<400> SEQUENCE: 5
ctctagagcg gccgccaccg                                                  20

<210> SEQ ID NO 6
<211> LENGTH: 24
<212> TYPE: DNA
<213> ORGANISM: Artificial Sequence
<220> FEATURE:
<223> OTHER INFORMATION: PCR primer 2 for plasmid

<400> SEQUENCE: 6
gcgttaatat tttgttaaaa ttcg                                             24

<210> SEQ ID NO 7
<211> LENGTH: 36
<212> TYPE: DNA
<213> ORGANISM: Artificial Sequence
<220> FEATURE:
<223> OTHER INFORMATION: PCR primer 3 for thioesterase

<400> SEQUENCE: 7
gcggccgctc tagaggaggg catctggact ccgcac                                36

<210> SEQ ID NO 8
<211> LENGTH: 36
<212> TYPE: DNA
<213> ORGANISM: Artificial Sequence
<220> FEATURE:
<223> OTHER INFORMATION: PCR primer 4 for thioesterase

<400> SEQUENCE: 8
gcggccgctc tagagatggc gctgagagac agacac                                36
```

<210> SEQ ID NO 9
<211> LENGTH: 36
<212> TYPE: DNA
<213> ORGANISM: Artificial Sequence
<220> FEATURE:
<223> OTHER INFORMATION: PCR primer 5 for thioesterase

<400> SEQUENCE: 9
cgcggtgttg cgcgcgaggg catctggact ccgcac         36

<210> SEQ ID NO 10
<211> LENGTH: 37
<212> TYPE: DNA
<213> ORGANISM: Artificial Sequence
<220> FEATURE:
<223> OTHER INFORMATION: PCR primer 6 for thioesterase

<400> SEQUENCE: 10
ctcttccaca gaagctcact tcttttttgac gatgtac        37

<210> SEQ ID NO 11
<211> LENGTH: 802
<212> TYPE: DNA
<213> ORGANISM: Artificial Sequence
<220> FEATURE:
<223> OTHER INFORMATION: VCP1 promoter

<400> SEQUENCE: 11
ggcggtcttt tgtcctttcc tctatagccc gcccgtctag agggcacacg cgatgatctt    60
tatatctctt catgtgtctt tgttttaact aggatactgc cgggtgaatg cccatcggac   120
aagaggccaa actctatcta caccctttttg acttctgttg tggtcgtagt gtgtgcttgc   180
atgccctgaa agtccaggca tcccacttgt gctctaaccc cattcaaaac agcagaagtg   240
cttaattaag atatagattc atgatctcct gtcccctcct tcttacccttt tcacaaacct   300 cacacagaag tctccactct tcgcctctaa aacctctttt taaattatgg taagttcgtg   360
cggcagtggg ttttcggatc tatatttgtc aagatccagt tcaaggtcag ggatgtagat   420
taagtacaga aggagaagca caagcgcgcc agttcgcccc tcacggcctg gagcagggca   480
tttaatccct ctatcttacc agaaccatac tatacaacca atcctgttgg catcgctctg   540
tctatttgtc gtgcgtgcat gtgtccatgg tgtggtgggg ggcaggggtt ttcggggttg   600
cggttgaagg caccttatca gaaagatgcc ctcagagata gaggtagccc cctccccccg   660
atcttcgacc agtcctgtca ggcgaacact ttcacccgtc gttcacctcg ttacacacaa   720
ggagtagacc tctgaagttc taattgtcat aaatgcccct ccccccctccc tctttcccctt   780 gatcctcccc tccgagcaga tt                                            802

<210> SEQ ID NO 12
<211> LENGTH: 99
<212> TYPE: DNA
<213> ORGANISM: Artificial Sequence
<220> FEATURE:
<223> OTHER INFORMATION: VCP1 chloroplast transit signal

<400> SEQUENCE: 12
atgaagaccg ccgctctcct cactgtctcc accctcatgg gcgcccaggc ctttatggcc    60
cccgccccca agttctcccg cacccgcggt gttgcgcgc                            99

<210> SEQ ID NO 13
<211> LENGTH: 643
<212> TYPE: DNA
<213> ORGANISM: Artificial Sequence
<220> FEATURE:
<223> OTHER INFORMATION: VCP1 terminator

<400> SEQUENCE: 13

```
gcttctgtgg aagagccagt ggtagtagca gtagcagcag cagtagcagc cgcagcactc    60
agtgttggcg cgagagattg tccatccctt cttaacctac cggaagagaa ataaggcctt   120
tctcccgtag ctgtcttcgt tgtttgtgc tgattgcttg atatgagagt gttgaattcc   180
tgcatcatgt ttttctctgt agtcctttcc taccccgtc attttctttt ctccctggtt   240
cttcttttgt caccttatt ttacataaaa ttttctttgt ttatagtgag aggaaggtag   300
agagggaaa acaagaacaa cgaacgcaag cgtgtgaaag gagggcgagt agaagagaaa   360
cagatctgtt gagcattgag agtggagccg ggggaaaggc ttgtgtgttg tctttgaaaa   420
agttgtttaa atcacgaatc cgttagttct catgtgtacc tctttcacta catgtgatgg   480
agaaaacaaa agtgtgagga ttaattgaag aaaaagaaga gttcgacacg tcaaaccgcc   540
caaaagacgt cacaaagaga acttgattct ctttgccgtg ttgatcctgt cttttccccc   600
agcttttctt gccacccgtg gcacacgaga tggacaagat cag                     643
```

<210> SEQ ID NO 14
<211> LENGTH: 37
<212> TYPE: DNA
<213> ORGANISM: Artificial Sequence
<220> FEATURE:
<223> OTHER INFORMATION: PCR primer 1 for VCP1 promoter

<400> SEQUENCE: 14

```
cgagctcggt acccgggcgg tcttttgtcc tttcctc                             37
```

<210> SEQ ID NO 15
<211> LENGTH: 22
<212> TYPE: DNA
<213> ORGANISM: Artificial Sequence
<220> FEATURE:
<223> OTHER INFORMATION: PCR primer 2 for VCP1 promoter

<400> SEQUENCE: 15

```
aatctgctcg gagggagga tc                                              22
```

<210> SEQ ID NO 16
<211> LENGTH: 36
<212> TYPE: DNA
<213> ORGANISM: Artificial Sequence
<220> FEATURE:
<223> OTHER INFORMATION: PCR primer 1 for VCP1 chloroplast transit
      signal

<400> SEQUENCE: 16

```
ccctccgagc agattatgaa gaccgccgct ctcctc                              36
```

<210> SEQ ID NO 17
<211> LENGTH: 28
<212> TYPE: DNA
<213> ORGANISM: Artificial Sequence
<220> FEATURE:
<223> OTHER INFORMATION: PCR primer 2 for VCP1 chloroplast transit
      signal

<400> SEQUENCE: 17
gcgcgcaaca ccgcgggtgc gggagaac                                    28

<210> SEQ ID NO 18
<211> LENGTH: 21
<212> TYPE: DNA
<213> ORGANISM: Artificial Sequence
<220> FEATURE:
<223> OTHER INFORMATION: PCR primer 1 for VCP1 terminator

<400> SEQUENCE: 18
gcttctgtgg aagagccagt g                                           21

<210> SEQ ID NO 19
<211> LENGTH: 35
<212> TYPE: DNA
<213> ORGANISM: Artificial Sequence
<220> FEATURE:
<223> OTHER INFORMATION: PCR primer 2 for VCP1 terminator

<400> SEQUENCE: 19
actctagagg atcccctgat cttgtccatc tcgtg                            35

<210> SEQ ID NO 20
<211> LENGTH: 20
<212> TYPE: DNA
<213> ORGANISM: Artificial Sequence
<220> FEATURE:
<223> OTHER INFORMATION: PCR primer 1 for plasmid pUC19

<400> SEQUENCE: 20
gggatcctct agagtcgacc                                             20

<210> SEQ ID NO 21
<211> LENGTH: 20
<212> TYPE: DNA
<213> ORGANISM: Artificial Sequence
<220> FEATURE:
<223> OTHER INFORMATION: PCR primer 2 for plasmid pUC19

<400> SEQUENCE: 21
cgggtaccga gctcgaattc                                             20

<210> SEQ ID NO 22
<211> LENGTH: 2093
<212> TYPE: DNA
<213> ORGANISM: Artificial Sequence
<220> FEATURE:
<223> OTHER INFORMATION: DNA fragment containing thioesterase

<400> SEQUENCE: 22
ggcggtcttt tgtcctttcc tctatagccc gcccgtctag agggcacacg cgatgatctt      60
tatatctctt catgtgtctt tgttttaact aggatactgc cgggtgaatg cccatcggac     120
aagaggccaa actctatcta cacccttttg acttctgttg tggtcgtagt gtgtgcttgc     180
atgccctgaa agtccaggca tcccacttgt gctctaaccc cattcaaaac agcagaagtg     240
cttaattaag atatagattc atgatctcct gtccctcct tcttacctttt tcacaaacct     300 cacacagaag tctccactct tcgcctctaa aacctctttt taaattatgg taagttcgtg     360
cggcagtggg ttttcggatc tatatttgtc aagatccagt tcaaggtcag ggatgtagat     420
taagtacaga aggagaagca caagcgcgcc agttcgcccc tcacggcctg gagcagggca     480
tttaatccct ctatcttacc agaaccatac tatacaacca atcctgttgg catcgctctg     540

```
tctatttgtc gtgcgtgcat gtgtccatgg tgtggtgggg ggcaggggtt ttcggggttg    600
cggttgaagg caccttatca gaaagatgcc ctcagagata gaggtagccc cctcccccg     660
atcttcgacc agtcctgtca ggcgaacact ttcacccgtc gttcacctcg ttacacacaa    720
ggagtagacc tctgaagttc taattgtcat aaatgcccct ccccctccc tctttcccctt    780
gatcctcccc tccgagcaga ttatgaagac cgccgctctc ctcactgtct ccaccctcat    840
ggcgcccag gcctttatgg cccccgcccc caagttctcc cgcacccgcg tgttgcgcg     900
cgagggcatc tggactccgc acctgggcga ggaggccaag ttgttgaacc tccagcgcga    960
gatggcgctg agagacagac acgacaagca atttgtgtgg cagacctgca gtggccaggg    1020
caaaattgag gactgccgca tatatcactg caagcgagaa gaagttgatc gtgaggtttc    1080
gctggacgcg ccggaaatgg tggagggcaa aacacggatt tgtgcagtga tgcgcgttgg    1140
cgacgagctg aacggccatc ctgggctttt gcatggcggc ttcactgccg ccgtgctgga    1200
cgatttcaca ggcctggcga cctggatgga gaagcaagcg caggcgctgg acaaggatgc    1260
ggccattttc accgctcaca tggatctcag ctatcggcga cccctgaagg cgaagtcgga    1320
gtacttggtt gaggtttgcg ttgaccgtgt tgagcggcaa aagaaggtct ttctgaatgc    1380
tgccatctat gacaaggaca gccatgcctg cgtgaaagca aaggtgttgt acatcgtcaa    1440
aaagaagtga gcttctgtgg aagagccagt ggtagtagca gtagcagcag cagtagcagc    1500
cgcagcactc agtgttggcg cgagagattg tccatccctt cttaacctac cggaagagaa    1560
ataaggcctt tctcccgtag ctgtcttcgt ttgtttgtgc tgattgcttg atatgagagt    1620
gttgaattcc tgcatcatgt ttttctctgt agtccttttcc taccccgtc attttctttt    1680
ctccctggtt cttcttttgt cacccttatt ttacataaaa ttttctttgt ttatagtgag    1740
aggaaggtag agaggggaaa acaagaacaa cgaacgcaag cgtgtgaaag gagggcgagt    1800
agaagagaaa cagatctgtt gagcattgag agtggagccg ggggaaaggc ttgtgtgttg    1860
tctttgaaaa agttgtttaa atcacgaatc cgttagttct catgtgtacc tctttcacta    1920
catgtgatgg agaaaacaaa agtgtgagga ttaattgaag aaaaagaaga gttcgacacg    1980
tcaaaccgcc caaagacgt cacaaagaga acttgattct ctttgccgtg ttgatcctgt    2040
cttttccccc agcttttctt gccacccgtg gcacacgaga tggacaagat cag            2093
```

<210> SEQ ID NO 23
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 23

```
atggccaagt tgaccagtgc cgttccggtg ctcaccgcgc gcgacgtcgc cggagcggtc     60
gagttctgga ccgaccggct cgggttctcc cgggacttcg tggaggacga cttcgccggt    120
gtggtccggg acgacgtgac cctgttcatc agcgcggtcc aggaccaggt ggtgccggac    180
aacaccctgg cctgggtgtg ggtgcgcggc ctggacgagc tgtacgccga gtggtcggag    240
gtcgtgtcca cgaacttccg ggacgcctcc gggccggcca tgaccgagat cggcgagcag    300
ccgtggggggc gggagttcgc cctgcgcgac ccggccggca actgcgtgca cttcgtggcc    360
gaggagcagg actaa                                                      375
```

```
<210> SEQ ID NO 24
<211> LENGTH: 500
<212> TYPE: DNA
<213> ORGANISM: Artificial Sequence
<220> FEATURE:
<223> OTHER INFORMATION: Tubulin promoter

<400> SEQUENCE: 24
actgcgcatg gattgaccga cggccggttg ccaacttttg gggtcggccc cccttttcta      60
gcccttgccc gtccagcaat taaaaattat caacggcata ccggcactgg aagcttcggg     120
tttacaattt tggcttgcct tcctaatact gtaccgcgga gaacgtatga tattacagaa     180
aaatgccttg cacagttagc gcaaagggaa aacgtttctc cgccattgta cttttttggaa    240 gagggaaagc gattgtaaaa tatggctctc cgctacgaga gtttgggctg ttgatacatg     300
tgaaaataag tgtggacgac tttgaatgac ttgatcaggc tgtttgcaca taaccagc      360 gcgcatgcac ttctgacatg tcaatgacga aatttcacac ttcaccaata aattgtatcc     420
ttacgttttg tctttctcac acgcacatat atgatcatag ataaaagcca atatcaagaa     480
gctgtctttt ttgtgaagca                                                 500

<210> SEQ ID NO 25
<211> LENGTH: 37
<212> TYPE: DNA
<213> ORGANISM: Artificial Sequence
<220> FEATURE:
<223> OTHER INFORMATION: PCR primer 1 for zeocin resistance gene

<400> SEQUENCE: 25
cttttttgtg aagcaatggc caagttgacc agtgccg                               37

<210> SEQ ID NO 26
<211> LENGTH: 37
<212> TYPE: DNA
<213> ORGANISM: Artificial Sequence
<220> FEATURE:
<223> OTHER INFORMATION: PCR primer 2 for zeocin resistance gene

<400> SEQUENCE: 26
ctcttccaca gaagcttagt cctgctcctc ggccacg                               37

<210> SEQ ID NO 27
<211> LENGTH: 35
<212> TYPE: DNA
<213> ORGANISM: Artificial Sequence
<220> FEATURE:
<223> OTHER INFORMATION: PCR primer 1 for tubulin promoter

<400> SEQUENCE: 27
cgagctcggt acccgactgc gcatggattg accga                                 35

<210> SEQ ID NO 28
<211> LENGTH: 28
<212> TYPE: DNA
<213> ORGANISM: Artificial Sequence
<220> FEATURE:
<223> OTHER INFORMATION: PCR primer 2 for tubulin promoter

<400> SEQUENCE: 28
tgcttcacaa aaagacagc ttcttgat                                          28
```

```
<210> SEQ ID NO 29
<211> LENGTH: 1518
<212> TYPE: DNA
<213> ORGANISM: Artificial Sequence
<220> FEATURE:
<223> OTHER INFORMATION: DNA fragment containing zeocin resistance gene

<400> SEQUENCE: 29
actgcgcatg gattgaccga cggccggttg ccaacttttg gggtcggccc cccttttcta      60
gcccttgccc gtccagcaat taaaaattat caacggcata ccggcactgg aagcttcggg     120
tttacaattt tggcttgcct tcctaatact gtaccgcgga aacgtatga tattacagaa     180
aaatgccttg cacagttagc gcaaagggaa aacgtttctc cgccattgta cttttttggaa    240
gagggaaagc gattgtaaaa tatggctctc cgctacgaga gtttgggctg ttgatacatg     300
tgaaaataag tgtggacgac tttgaatgac ttgatcaggc tgtttgcaca tataaccagc     360
gcgcatgcac ttctgacatg tcaatgacga aatttcacac ttcaccaata aattgtatcc     420
ttacgttttg tctttctcac acgcacatat atgatcatag ataaaagcca atatcaagaa     480
gctgtctttt ttgtgaagca atggccaagt tgaccagtgc cgttccggtg ctcaccgcgc     540
gcgacgtcgc cggagcggtc gagttctgga ccgaccggct cgggttctcc cgggacttcg     600
tggaggacga cttcgccggt gtggtccggg acgacgtgac cctgttcatc agcgcggtcc     660
aggaccaggt ggtgccggac aacaccctgg cctgggtgtg gtgcgcggc ctggacgagc     720
tgtacgccga gtggtcggag tcgtgtccca cgaacttccg ggacgcctcc gggccggcca    780
tgaccgagat cggcgagcag ccgtgggggc gggagttcgc cctgcgcgac ccggccggca     840
actgcgtgca cttcgtggcc gaggagcagg actaagcttc tgtggaagag ccagtggtag     900
tagcagtagc agcagcagta gcagccgcag cactcagtgt tggcgcgaga gattgtccat     960
cccttcttaa cctaccggaa gagaaataag gcctttctcc cgtagctgtc ttcgtttgtt    1020
tgtgctgatt gcttgatatg agagtgttga attcctgcat catgttttc tctgtagtcc     1080
tttcctaccc ccgtcatttt cttttctccc tggttcttct tttgtcaccc ttattttaca    1140
taaaattttc tttgtttata gtgagaggaa ggtagagagg ggaaaacaag aacaacgaac    1200
gcaagcgtgt gaaaggaggg cgagtagaag agaaacagat ctgttgagca ttgagagtgg    1260
agccgggga aaggcttgtg tgttgtcttt gaaaaagttg tttaaatcac gaatccgtta    1320
gttctcatgt gtacctcttt cactacatgt gatggagaaa acaaaagtgt gaggattaat    1380
tgaagaaaaa gaagagttcg acacgtcaaa ccgcccaaaa gacgtcacaa agagaacttg    1440
attctctttg ccgtgttgat cctgtctttt ccccccagctt tcttgccac ccgtggcaca     1500
cgagatggac aagatcag                                                  1518

<210> SEQ ID NO 30
<211> LENGTH: 22
<212> TYPE: DNA
<213> ORGANISM: Artificial Sequence
<220> FEATURE:
<223> OTHER INFORMATION: PCR primer 1 for DNA fragment containing
      thioesterase

<400> SEQUENCE: 30 ggcggtctttt tgtcctttcc tc                                              22

<210> SEQ ID NO 31
<211> LENGTH: 20
<212> TYPE: DNA
<213> ORGANISM: Artificial Sequence
```

```
<220> FEATURE:
<223> OTHER INFORMATION: PCR primer 2 for DNA fragment containing
      thioesterase

<400> SEQUENCE: 31
ctgatcttgt ccatctcgtg                                               20

<210> SEQ ID NO 32
<211> LENGTH: 20
<212> TYPE: DNA
<213> ORGANISM: Artificial Sequence
<220> FEATURE:
<223> OTHER INFORMATION: PCR primer 2 for DNA fragment containing zeocin
      resistance gene

<400> SEQUENCE: 32
actgcgcatg gattgaccga                                               20

<210> SEQ ID NO 33
<211> LENGTH: 167
<212> TYPE: PRT
<213> ORGANISM: Artificial Sequence
<220> FEATURE:
<223> OTHER INFORMATION: thioesterase mutant

<400> SEQUENCE: 33

Met Asn Glu Arg Arg Glu Glu Ile Leu Gly Asn Arg Lys Asp Lys Gln
1               5                   10                  15

Phe Ile Trp Gln Thr Cys Thr Gly Pro Arg Arg Ile Glu Glu Cys Arg
            20                  25                  30

Ile Phe His Cys Arg Arg Gly Asp Val Asp Arg Glu Val Ser Leu Asp
        35                  40                  45

Gly Pro Glu Ala Val Gly Lys Thr Arg Ile Cys Cys Val Ile Lys
    50                  55                  60

Val Gly Asp Glu Leu Asn Gly His Pro Gly Leu Leu His Gly Gly Phe
65                  70                  75                  80

Ser Ala Ala Ile Ile Asp Asp Phe Thr Gly Leu Ala Thr Trp Met Glu
                85                  90                  95

Lys Asp Ala Gln Asp Val Gly Lys Asp Val Lys Ile Phe Thr Ala His
            100                 105                 110

Leu Asp Leu Ser Tyr Arg Arg Pro Leu Arg Ser Asn Ser Glu Tyr Leu
        115                 120                 125

Val Glu Val Cys Val Asp Val Glu Arg Gly Lys Lys Val Phe Leu
    130                 135                 140

Asn Ala Ala Ile Tyr Asp Asp Ser Asp His Ala Cys Val Lys Gly Arg
145                 150                 155                 160

Ala Leu Tyr Ile Ile Lys Ala
                165

<210> SEQ ID NO 34
<211> LENGTH: 504
<212> TYPE: DNA
<213> ORGANISM: Artificial Sequence
<220> FEATURE:
<223> OTHER INFORMATION: thioesterase mutant

<400> SEQUENCE: 34
atgaacgagc ggagggagga gatacttggc aaccgaaaag acaaacagtt catttggcag     60
acctgcaccg ggccacgacg aattgaggag tgccgtatat ttcactgtcg ccgcggtgat    120
gtcgatcgcg aagtttcctt agatgggcca gaagccgtgg aaggcaagac cagaatttgc    180
```

```
tgcgtcatca aggttggtga cgagctgaat ggtcatcccg gtttgctgca tggaggcttc    240
tcggcagcta tcatcgacga tttcaccggg ttggcgacat ggatggagaa ggacgcccag    300
gacgtgggca aggacgtgaa gatctttacg gcccatcttg acctcagcta ccggcgacct    360
ttgagatcaa actcggagta cttggtggag gtatgcgtgg atcgtgtcga gcgtgggaag    420
aaagtattcc taaacgctgc aatctatgac gactctgacc atgcgtgcgt caaagggcgc    480
gcgctgtata taatcaaagc ctga                                           504

<210> SEQ ID NO 35
<211> LENGTH: 37
<212> TYPE: DNA
<213> ORGANISM: Artificial Sequence
<220> FEATURE:
<223> OTHER INFORMATION: PCR primer 1 for thioesterase mutant

<400> SEQUENCE: 35
gcggccgctc tagagaacga gcggagggag gagatac                              37

<210> SEQ ID NO 36
<211> LENGTH: 39
<212> TYPE: DNA
<213> ORGANISM: Artificial Sequence
<220> FEATURE:
<223> OTHER INFORMATION: PCR primer 2 for thioesterase mutant

<400> SEQUENCE: 36
acaaaatatt aacgcgtcgt catagattgc agcgtttag                            39
```